(12) United States Patent
Shirakawa et al.

(10) Patent No.: US 11,666,646 B2
(45) Date of Patent: Jun. 6, 2023

(54) CANCER THERAPY UTILIZING COMBINATION OF ORAL TUMOR VACCINE AND IMMUNOSUPPRESSION INHIBITOR

(71) Applicants: NATIONAL UNIVERSITY CORPORATION KOBE UNIVERSITY, Hyogo (JP); OSAKA UNIVERSITY, Osaka (JP)

(72) Inventors: Toshiro Shirakawa, Hyogo (JP); Yoshiko Hashii, Osaka (JP)

(73) Assignees: NATIONAL UNIVERSITY CORPORATION KOBE UNIVERSITY, Hyogo (JP); OSAKA UNIVERSITY, Osaka (JP)

( * ) Notice: Subject to any disclaimer, the term of this patent is extended or adjusted under 35 U.S.C. 154(b) by 821 days.

(21) Appl. No.: 16/472,210

(22) PCT Filed: Dec. 8, 2017

(86) PCT No.: PCT/JP2017/044123
§ 371 (c)(1),
(2) Date: Jun. 21, 2019

(87) PCT Pub. No.: WO2018/123507
PCT Pub. Date: Jul. 5, 2018

(65) Prior Publication Data
US 2019/0351038 A1 Nov. 21, 2019

(30) Foreign Application Priority Data
Dec. 26, 2016 (JP) .............................. JP2016-250560

(51) Int. Cl.
A61K 35/745 (2015.01)
A61K 39/00 (2006.01)
A61P 35/00 (2006.01)

(52) U.S. Cl.
CPC .... *A61K 39/001153* (2018.08); *A61K 35/745* (2013.01); *A61K 39/001102* (2018.08); *A61P 35/00* (2018.01); *A61K 2039/523* (2013.01); *A61K 2039/542* (2013.01)

(58) Field of Classification Search
None
See application file for complete search history.

(56) References Cited

U.S. PATENT DOCUMENTS

| | | | |
|---|---|---|---|
| 7,553,636 | B2 | 6/2009 | Sung et al. |
| 8,354,113 | B2 | 1/2013 | Shirakawa et al. |
| 2010/0247556 | A1 | 9/2010 | Sugiyama |
| 2016/0008459 | A1 | 1/2016 | Shirakawa et al. |
| 2017/0224791 | A1 | 8/2017 | Okamura et al. |
| 2018/0169156 | A1 | 6/2018 | Shirakawa et al. |

FOREIGN PATENT DOCUMENTS

| | | |
|---|---|---|
| JP | 2005500054 A | 1/2005 |
| JP | 5187642 B2 | 4/2013 |
| JP | 5561681 B2 | 7/2014 |
| JP | 5714619 B2 | 5/2015 |
| WO | WO2014/129412 * | 8/2014 |
| WO | 2014144885 A2 | 9/2014 |
| WO | 2016091487 A1 | 6/2016 |
| WO | 2016196605 A1 | 12/2016 |

OTHER PUBLICATIONS

Buckler et al. (Molecular and Cellular Biology vol. No. 3, pp. 1707-1712, Mar. 1991).*
Google Translation of WO 2014129412.*
Extended European Search Report issued in corresponding European Patent Application No. 17887332.9 dated Sep. 11, 2020 (11 pages).
Goto et al, "DSP-7888, a Novel Cocktail Design of WT1 Peptide Vaccine, and Its Combinational Immunotherapy with Immune Checkpoint-Blocking Antibody Against PD-1," Blood, Dec. 2, 2016, vol. 128, No. 22, pp. 1-7.
Anonymous, "SELLAS Life Sciences Group Announces Initiation of Galinpepimul-S (WT1 Cancer Vaccine) Phase 1 Clinical Trial in Combination with PD-1 Checkpoint Inhibitor for Patients with Ovarian Cancer," May 2, 2016, https://www.sellaslifesciences.com/investors/news/News-Details/2016/SELLAS-Life-Sciences-Group-Announces-Initiation-of-Galinpepimut-S-WT1-Cancer-Vaccine-Phase-1-Clinical-Trial-in-Combination-with-PD-1-Checkpoint-Inhibitor-for-Patients-with-Ovarian-Cancer/default.aspx, pp. 1-3.
Gaillard et al, "The role of immune checkpoint inhibition in the treatment of ovarian cancer," Gynecologic Oncology Research and Practice, 2016, vol. 3, No. 11, pp. 1-14.
Final Office Action issued in corresponding U.S. Appl. No. 15/737,758 dated Mar. 4, 2020 (7 pages).
International Search Report and Written Opinion issued in corresponding International Patent Application No. PCT/JP2017/044123 (with English translation of International Search Report) dated Jan. 16, 2018 (11 pages).
Karaki et al., "Is There Still Room for Cancer Vaccines at the Era of Checkpoint Inhibitors," Vaccines, 2016, 4, 37; doi:10.3390/vaccines4040037, pp. 1-21.
Kitagawa et al., "Development of the Novel Oral Tumor Vaccine Using Bifidobacterium longum Displaying Wilms' Tumor 1 Protein," Molecular Therapy, 2016, vol. 24, Supplement 1, p. S157, left col. (395), (2 pages).

(Continued)

*Primary Examiner* — Jennifer E Graser
(74) *Attorney, Agent, or Firm* — Kilyk & Bowersox, P.L.L.C.

(57) ABSTRACT

It is an object to provide a combination therapy effective in cancer immunotherapy. The object is achieved by providing an anti-tumor agent, including a transformed *Bifidobacterium* containing DNA encoding a WT1 protein and DNA encoding a GNB/LNB substrate-binding membrane protein derived from a *Bifidobacterium*, the transformed *Bifidobacterium* being designed to display the WT1 protein as an antigen on a surface of the transformed *Bifidobacterium*, the anti-tumor agent being for use in combination with an immunosuppression inhibitor. The transformed *Bifidobacterium* can be used as an oral tumor vaccine.

20 Claims, 17 Drawing Sheets
Specification includes a Sequence Listing.

(56) References Cited

OTHER PUBLICATIONS

Nakatsuka et al., "Immunohistochemical detection of WT1 protein in a variety of cancer cells," Modern Pathology, 2006, 19, pp. 804-814.

Sugiyama, H., "WT1 (Wilms' Tumor Gene 1): Biology and Cancer Immunotherapy," Jpn J Clin Oncol, 2010, 40(5), pp. 377-387.

\* cited by examiner

*B. longum* 2012(EXPRESSING GL-BP) : 46kDa
*B. longum* 410(EXPRESSING SHORT GL-BP-WT1) : 72.65kDa
*B. longum* 420(EXPRESSING LONG GL-BP-WT1) : 82.97kDa

SEQUENCE LISTING

<160> NUMBER OF SEQ ID NOS: 26

<210> SEQ ID NO 1
<211> LENGTH: 323
<212> TYPE: PRT
<213> ORGANISM: Mus musculus

<400> SEQUENCE: 1

```
Pro Ser Gln Ala Ser Ser Gly Gln Ala Arg Met Phe Pro Asn Ala Pro
1               5                   10                  15

Tyr Leu Pro Ser Cys Leu Glu Ser Gln Pro Thr Ile Arg Asn Gln Gly
            20                  25                  30

Tyr Ser Thr Val Thr Phe Asp Gly Ala Pro Ser Tyr Gly His Thr Pro
        35                  40                  45

Ser His His Ala Ala Gln Phe Pro Asn His Ser Phe Lys His Glu Asp
    50                  55                  60

Pro Met Gly Gln Gln Gly Ser Leu Gly Glu Gln Gln Tyr Ser Val Pro
65                  70                  75                  80

Pro Pro Val Tyr Gly Cys His Thr Pro Thr Asp Ser Cys Thr Gly Ser
                85                  90                  95

Gln Ala Leu Leu Leu Arg Thr Pro Tyr Ser Ser Asp Asn Leu Tyr Gln
            100                 105                 110

Met Thr Ser Gln Leu Glu Cys Met Thr Trp Asn Gln Met Asn Leu Gly
        115                 120                 125

Ala Thr Leu Lys Gly Met Ala Ala Gly Ser Ser Ser Ser Val Lys Trp
    130                 135                 140

Thr Glu Gly Gln Ser Asn His Gly Ile Gly Tyr Glu Ser Glu Asn His
145                 150                 155                 160

Thr Ala Pro Ile Leu Cys Gly Ala Gln Tyr Arg Ile His Thr His Gly
                165                 170                 175

Val Phe Arg Gly Ile Gln Asp Val Arg Arg Val Ser Gly Val Ala Pro
            180                 185                 190

Thr Leu Val Arg Ser Ala Ser Glu Thr Ser Glu Lys Arg Pro Phe Met
        195                 200                 205

Cys Ala Tyr Pro Gly Cys Asn Lys Arg Tyr Phe Lys Leu Ser His Leu
    210                 215                 220

Gln Met His Ser Arg Lys His Thr Gly Glu Lys Pro Tyr Gln Cys Asp
225                 230                 235                 240

Phe Lys Asp Cys Glu Arg Arg Phe Ser Arg Ser Asp Gln Leu Lys Arg
                245                 250                 255

His Gln Arg Arg His Thr Gly Val Lys Pro Phe Gln Cys Lys Thr Cys
            260                 265                 270

Gln Arg Lys Phe Ser Arg Ser Asp His Leu Lys Thr His Thr Arg Thr
        275                 280                 285

His Thr Gly Lys Thr Ser Glu Lys Pro Phe Ser Cys Arg Trp His Ser
    290                 295                 300

Cys Gln Lys Lys Phe Ala Arg Ser Asp Glu Leu Val Arg His His Asn
305                 310                 315                 320

Met His Gln
```

<210> SEQ ID NO 2
<211> LENGTH: 985
<212> TYPE: DNA
<213> ORGANISM: Mus musculus

<400> SEQUENCE: 2

```
ctcgagccgt cccaggcgtc gtcgggccag gcgaggatgt cccgaacgc gccctacctg      60
cccagctgcc tggagtccca gccgacgatc cgcaaccagg gctactccac cgtgacgttc     120
gacggcgccc cgtcctacgg ccacacgccc agccaccacg ccgcccagtt cccgaaccac     180
agcttcaagc acgaagaccc catgggccag cagggcagcc tcggcgaaca gcagtacagc     240
gtgccgccgc cggtctacgg ctgccacacc ccgaccgact cctgcacggg ctcccaggcc     300
ctgctcctgc gtacgccgta ctcctccgac aacctctacc agatgacctc ccagctggag     360
tgcatgacct ggaaccagat gaacctgggc gccacgctga agggaatggc cgcggggtcg     420
tcgagctccg tcaagtggac cgaaggccag tccaaccacg gcatcggcta cgagtccgag     480
aaccacaccg cgccgatcct gtgcggagcc cagtaccgca tccacacgca cggcgtcttc     540
cgcggcatcc aggacgtccg gcgcgtctcc ggcgtcgcgc cgaccctggt gcggtccgcc     600
tccgagacct ccgagaagcg cccgttcatg tgcgcctacc cgggctgcaa caagcgctac     660
ttcaagctct cgcacctgca gatgcactcc cggaagcaca ccggcgagaa gccgtaccag     720
tgcgacttca aggactgcga acgccgcttc tcgcgcagcg accagctgaa gcgccaccag     780
cgtaggcaca ccggcgtgaa gcccttccag tgcaagacct gccagcgcaa gttctcccgc     840
agcgaccacc tcaagacgca cacccgcacc cacaccggca agacgtccga gaagccgttc     900
tcgtgccgct ggcacagctg ccagaagaag ttcgcccgca gcgacgagct cgtgcgccac     960
cacaacatgc accagtgaag catgc                                            985
```

<210> SEQ ID NO 3
<211> LENGTH: 22
<212> TYPE: DNA
<213> ORGANISM: Artificial
<220> FEATURE:
<223> OTHER INFORMATION: Primer for GL-BP (glt-f)

<400> SEQUENCE: 3

```
ggggtgctga tatattggtt tg                                               22
```

<210> SEQ ID NO 4
<211> LENGTH: 31
<212> TYPE: DNA
<213> ORGANISM: Artificial
<220> FEATURE:
<223> OTHER INFORMATION: Primer for GL-BP (glt-r)

<400> SEQUENCE: 4

```
gctcgagctc ggaaacagac aggccgaagt t                                     31
```

<210> SEQ ID NO 5
<211> LENGTH: 6
<212> TYPE: DNA
<213> ORGANISM: Artificial
<220> FEATURE:
<223> OTHER INFORMATION: Recognition sequence for XhoI

<400> SEQUENCE: 5

```
ctcgag                                                                  6
```

```
<210> SEQ ID NO 6
<211> LENGTH: 6
<212> TYPE: DNA
<213> ORGANISM: Artificial
<220> FEATURE:
<223> OTHER INFORMATION: Recognition sequence for SphI

<400> SEQUENCE: 6 gcatgc                                                                    6

<210> SEQ ID NO 7
<211> LENGTH: 24
<212> TYPE: DNA
<213> ORGANISM: Artificial
<220> FEATURE:
<223> OTHER INFORMATION: Primer for WT1 (WT1-f)

<400> SEQUENCE: 7
cgctcgagcc gtcccaggcg tcgt                                               24

<210> SEQ ID NO 8
<211> LENGTH: 30
<212> TYPE: DNA
<213> ORGANISM: Artificial
<220> FEATURE:
<223> OTHER INFORMATION: Primer for WT1 (WT1-r2)

<400> SEQUENCE: 8
gcgcatgctc actcgccggt gtgcttccgg                                         30

<210> SEQ ID NO 9
<211> LENGTH: 36
<212> TYPE: DNA
<213> ORGANISM: Artificial
<220> FEATURE:
<223> OTHER INFORMATION: Primer  (Infusion-F)

<400> SEQUENCE: 9
ggaaaactgt ccatagatgg cgaggcgaac gccacg                                  36

<210> SEQ ID NO 10
<211> LENGTH: 36
<212> TYPE: DNA
<213> ORGANISM: Artificial
<220> FEATURE:
<223> OTHER INFORMATION: Primer  (Infusion-R)

<400> SEQUENCE: 10
tttcatctgt gcatagtgct gcaaggcgat taagtt                                  36

<210> SEQ ID NO 11
<211> LENGTH: 23
<212> TYPE: DNA
<213> ORGANISM: Artificial
<220> FEATURE:
<223> OTHER INFORMATION: Primer  (410, 420-F)

<400> SEQUENCE: 11
acgatccgca accagggcta ctc                                                23

<210> SEQ ID NO 12
<211> LENGTH: 23
<212> TYPE: DNA
<213> ORGANISM: Artificial
<220> FEATURE:
<223> OTHER INFORMATION: Primer  (410-R)
```

<400> SEQUENCE: 12
ggtgcgagag cttgaagtag cgc                                         23

<210> SEQ ID NO 13
<211> LENGTH: 22
<212> TYPE: DNA
<213> ORGANISM: Artificial
<220> FEATURE:
<223> OTHER INFORMATION: Primer (420-R)

<400> SEQUENCE: 13
gtcgctgcgg gcgaacttct tc                                          22

<210> SEQ ID NO 14
<211> LENGTH: 323
<212> TYPE: PRT
<213> ORGANISM: Homo sapiens

<400> SEQUENCE: 14

Pro Ser Gln Ala Ser Ser Gly Gln Ala Arg Met Phe Pro Asn Ala Pro
1               5                   10                  15

Tyr Leu Pro Ser Cys Leu Glu Ser Gln Pro Ala Ile Arg Asn Gln Gly
            20                  25                  30

Tyr Ser Thr Val Thr Phe Asp Gly Thr Pro Ser Tyr Gly His Thr Pro
        35                  40                  45

Ser His His Ala Ala Gln Phe Pro Asn His Ser Phe Lys His Glu Asp
    50                  55                  60

Pro Met Gly Gln Gln Gly Ser Leu Gly Glu Gln Gln Tyr Ser Val Pro
65                  70                  75                  80

Pro Pro Val Tyr Gly Cys His Thr Pro Thr Asp Ser Cys Thr Gly Ser
                85                  90                  95

Gln Ala Leu Leu Leu Arg Thr Pro Tyr Ser Ser Asp Asn Leu Tyr Gln
            100                 105                 110

Met Thr Ser Gln Leu Glu Cys Met Thr Trp Asn Gln Met Asn Leu Gly
        115                 120                 125

Ala Thr Leu Lys Gly Val Ala Ala Gly Ser Ser Ser Ser Val Lys Trp
    130                 135                 140

Thr Glu Gly Gln Ser Asn His Ser Thr Gly Tyr Glu Ser Asp Asn His
145                 150                 155                 160

Thr Thr Pro Ile Leu Cys Gly Ala Gln Tyr Arg Ile His Thr His Gly
                165                 170                 175

Val Phe Arg Gly Ile Gln Asp Val Arg Arg Val Pro Gly Val Ala Pro
            180                 185                 190

Thr Leu Val Arg Ser Ala Ser Glu Thr Ser Glu Lys Arg Pro Phe Met
        195                 200                 205

Cys Ala Tyr Pro Gly Cys Asn Lys Arg Tyr Phe Lys Leu Ser His Leu
    210                 215                 220

Gln Met His Ser Arg Lys His Thr Gly Glu Lys Pro Tyr Gln Cys Asp
225                 230                 235                 240

Phe Lys Asp Cys Glu Arg Arg Phe Ser Arg Ser Asp Gln Leu Lys Arg
                245                 250                 255

His Gln Arg Arg His Thr Gly Val Lys Pro Phe Gln Cys Lys Thr Cys
            260                 265                 270

Gln Arg Lys Phe Ser Arg Ser Asp His Leu Lys Thr His Thr Arg Thr
        275                 280                 285

```
His Thr Gly Lys Thr Ser Glu Lys Pro Phe Ser Cys Arg Trp Pro Ser
    290                 295                 300
Cys Gln Lys Lys Phe Ala Arg Ser Asp Glu Leu Val Arg His His Asn
305                 310                 315                 320
Met His Gln
```

<210> SEQ ID NO 15
<211> LENGTH: 973
<212> TYPE: DNA
<213> ORGANISM: Homo sapiens

<400> SEQUENCE: 15

```
ccgtcccagg cgtcgtcggg ccaggcgagg atgttcccga acgcgcccta cctgcccagc      60
tgcctggagt cccagccggc gatccgcaac cagggctact ccaccgtgac gttcgacggc     120
accccgtcct acggccacac gcccagccac acgccgccc  agttcccgaa ccacagcttc     180
aagcacgaag accccatggg ccagcagggc agcctcggcg aacagcagta cagcgtgccg     240
ccgccggtct acggctgcca cacccccgac gactcctgca cgggctccca ggccctgctc     300
ctgcgtacgc cgtactcctc cgacaacctc taccagatga cctcccagct ggagtgcatg     360
acctggaacc agatgaacct gggcgccacg ctgaagggga tcgccgcggg gtcgtcgagc     420
tccgtcaagt ggaccgaagg ccagtccaac cactccaccg gctacgagtc cgacaaccac     480
accacgccga tcctgtgcgg agcccagtac cgcatccaca cgcacggcgt cttccgcggc     540
atccaggacg tccggcgcgt ccccggcgtc gcgccgaccc tggtgcggtc cgcctccgag     600
acctccgaga agcccccgtt catgtgcgcc tacccgggct gcaacaagcg ctacttcaag     660
ctctcgcacc tgcagatgca ctcccggaag cacaccggcg agaagccgta ccagtgcgac     720
ttcaaggact gcgaacgccg cttctcgcgc agcgaccagc tgaagcgcca ccagcgtagg     780
cacaccggcg tgaagccctt ccagtgcaag acctgccagc gcaagttctc ccgcagcgac     840
cacctcaaga cgcacacccg cacccacacc ggcaagacgt ccgagaagcc gttctcgtgc     900
cgctggccca gctgccagaa gaagttcgcc cgcagcgacg agctcgtgcg ccaccacaac     960
atgcaccagt gaa                                                        973
```

<210> SEQ ID NO 16
<211> LENGTH: 323
<212> TYPE: PRT
<213> ORGANISM: Homo sapiens

<400> SEQUENCE: 16

```
Pro Ser Gln Ala Ser Ser Gly Gln Ala Arg Met Phe Pro Asn Ala Pro
1               5                   10                  15
Tyr Leu Pro Ser Cys Leu Glu Ser Gln Pro Ala Ile Arg Asn Gln Gly
            20                  25                  30
Tyr Ser Thr Val Thr Phe Asp Gly Thr Pro Ser Tyr Gly His Thr Pro
        35                  40                  45
Ser His His Ala Ala Gln Phe Pro Asn His Ser Phe Lys His Glu Asp
    50                  55                  60
Pro Met Gly Gln Gln Gly Ser Leu Gly Glu Gln Gln Tyr Ser Val Pro
65                  70                  75                  80
Pro Pro Val Tyr Gly Cys His Thr Pro Thr Asp Ser Cys Thr Gly Ser
                85                  90                  95
Gln Ala Leu Leu Leu Arg Thr Pro Tyr Ser Ser Asp Asn Leu Tyr Gln
            100                 105                 110
```

```
Met Thr Ser Gln Leu Glu Cys Tyr Thr Trp Asn Gln Met Asn Leu Gly
            115                 120                 125
Ala Thr Leu Lys Gly Val Ala Ala Gly Ser Ser Ser Val Lys Trp
130                 135                 140
Thr Glu Gly Gln Ser Asn His Ser Thr Gly Tyr Glu Ser Asp Asn His
145                 150                 155                 160
Thr Thr Pro Ile Leu Cys Gly Ala Gln Tyr Arg Ile His Thr His Gly
                165                 170                 175
Val Phe Arg Gly Ile Gln Asp Val Arg Arg Val Pro Gly Val Ala Pro
            180                 185                 190
Thr Leu Val Arg Ser Ala Ser Glu Thr Ser Glu Lys Arg Pro Phe Met
        195                 200                 205
Cys Ala Tyr Pro Gly Cys Asn Lys Arg Tyr Phe Lys Leu Ser His Leu
    210                 215                 220
Gln Met His Ser Arg Lys His Thr Gly Glu Lys Pro Tyr Gln Cys Asp
225                 230                 235                 240
Phe Lys Asp Cys Glu Arg Arg Phe Ser Arg Ser Asp Gln Leu Lys Arg
                245                 250                 255
His Gln Arg Arg His Thr Gly Val Lys Pro Phe Gln Cys Lys Thr Cys
            260                 265                 270
Gln Arg Lys Phe Ser Arg Ser Asp His Leu Lys Thr His Thr Arg Thr
        275                 280                 285
His Thr Gly Lys Thr Ser Glu Lys Pro Phe Ser Cys Arg Trp Pro Ser
    290                 295                 300
Cys Gln Lys Lys Phe Ala Arg Ser Asp Glu Leu Val Arg His His Asn
305                 310                 315                 320
Met His Gln
```

<210> SEQ ID NO 17
<211> LENGTH: 973
<212> TYPE: DNA
<213> ORGANISM: Homo sapiens

<400> SEQUENCE: 17

```
ccgtcccagg cgtcgtcggg ccaggcgagg atgttcccga acgcgcccta cctgcccagc      60
tgcctggagt cccagccggc gatccgcaac cagggctact ccaccgtgac gttcgacggc     120
accccgtcct acggccacac gcccagccac acgccgccc agttcccgaa ccacagcttc     180
aagcacgaag accccatggg ccagcagggc agcctcggcg aacagcagta cagcgtgccg     240
ccgccggtct acggctgcca caccccgacc gactcctgca cgggctccca ggccctgctc     300
ctgcgtacgc cgtactcctc cgacaacctc taccagatga cctcccagct ggagtgctac     360
acctggaacc agatgaacct gggcgccacg ctgaagggag tcgccgcggg gtcgtcgagc     420
tccgtcaagt ggaccgaagg ccagtccaac cactccaccg gctacgagtc cgacaaccac     480
accacgccga tcctgtgcgg agcccagtac cgcatccaca cgcacggcgt cttccgcggc     540
atccaggacg tccggcgcgt cccccggcgtc gcgccgaccc tggtgcggtc cgcctccgag     600
acctccgaga agcgcccgtt catgtgcgcc tacccgggct gcaacaagcg ctacttcaag     660
ctctcgcacc tgcagatgca ctcccggaag cacaccggcg agaagccgta ccagtgcgac     720
ttcaaggact gcgaacgccg cttctcgcgc agcgaccagc tgaagcgcca ccagcgtagg     780
cacaccggcg tgaagccctt ccagtgcaag acctgccagc gcaagttctc ccgcagcgac     840
cacctcaaga cgcacacccg cacccacacc ggcaagacgt ccgagaagcc gttctcgtgc     900
```

```
cgctggccca gctgccagaa gaagttcgcc cgcagcgacg agctcgtgcg ccaccacaac    960
atgcaccagt gaa                                                        973
```

<210> SEQ ID NO 18
<211> LENGTH: 16
<212> TYPE: PRT
<213> ORGANISM: Artificial Sequence
<220> FEATURE:
<223> OTHER INFORMATION: T cell epitope np332

<400> SEQUENCE: 18

Lys Arg Tyr Phe Lys Leu Ser His Leu Gln Met His Ser Arg Lys His
1               5                   10                  15

<210> SEQ ID NO 19
<211> LENGTH: 9
<212> TYPE: PRT
<213> ORGANISM: Artificial Sequence
<220> FEATURE:
<223> OTHER INFORMATION: T cell epitope np126

<400> SEQUENCE: 19

Arg Met Phe Pro Asn Ala Pro Tyr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: T cell epitope n187

<400> SEQUENCE: 20

Ser Leu Gly Glu Gln Gln Tyr Ser Val
1               5

<210> SEQ ID NO 21
<211> LENGTH: 9
<212> TYPE: PRT
<213> ORGANISM: Artificial Sequence
<220> FEATURE:
<223> OTHER INFORMATION: T cell epitope n235

<400> SEQUENCE: 21

Cys Met Thr Trp Asn Gln Met Asn Leu
1               5

<210> SEQ ID NO 22
<211> LENGTH: 449
<212> TYPE: PRT
<213> ORGANISM: Mus musculus

<400> SEQUENCE: 22

Met Gly Ser Asp Val Arg Asp Leu Asn Ala Leu Leu Pro Ala Val Ser
1               5                   10                  15

Ser Leu Gly Gly Gly Gly Gly Cys Gly Leu Pro Val Ser Gly Ala
                20                  25                  30

Arg Gln Trp Ala Pro Val Leu Asp Phe Ala Pro Pro Gly Ala Ser Ala
            35                  40                  45

Tyr Gly Ser Leu Gly Gly Pro Ala Pro Pro Ala Pro Pro Pro
        50                  55                  60

Pro Pro Pro Pro His Ser Phe Ile Lys Gln Glu Pro Ser Trp Gly Gly
65                  70                  75                  80

```
Ala Glu Pro His Glu Glu Gln Cys Leu Ser Ala Phe Thr Leu His Phe
             85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Thr Ile
    130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
            260                 265                 270

Ser Glu Asn His Thr Ala Pro Ile Leu Cys Gly Ala Gln Tyr Arg Ile
        275                 280                 285

His Thr His Gly Val Phe Arg Gly Ile Gln Asp Val Arg Arg Val Ser
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
        435                 440                 445

Leu

<210> SEQ ID NO 23
<211> LENGTH: 449
<212> TYPE: PRT
<213> ORGANISM: Homo sapiens

<400> SEQUENCE: 23
```

```
Met Gly Ser Asp Val Arg Asp Leu Asn Ala Leu Leu Pro Ala Val Pro
1               5                   10                  15

Ser Leu Gly Gly Gly Gly Cys Ala Leu Pro Val Ser Gly Ala Ala
        20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
50                  55                  60

Pro Pro Pro His Ser Phe Ile Lys Gln Pro Ser Trp Gly Gly
65              70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
            165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
            245                 250                 255

Ser Val Lys Trp Thr Glu Gly Gln Ser Asn His Ser Thr Gly Tyr Glu
        260                 265                 270

Ser Asp Asn His Thr Thr Pro Ile Leu Cys Gly Ala Gln Tyr Arg Ile
    275                 280                 285

His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
            325                 330                 335

Leu Ser His Leu Gln Met His Ser Arg Lys His Thr Gly Glu Lys Pro
        340                 345                 350

Tyr Gln Cys Asp Phe Lys Asp Cys Glu Arg Arg Phe Ser Arg Ser Asp
    355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
            405                 410                 415

Arg Trp Pro Ser Cys Gln Lys Lys Phe Ala Arg Ser Asp Glu Leu Val
```

```
                420             425             430
Arg His His Asn Met His Gln Arg Asn Met Thr Lys Leu Gln Leu Ala
        435             440             445

Leu

<210> SEQ ID NO 24
<211> LENGTH: 30
<212> TYPE: DNA
<213> ORGANISM: Artificial Sequence
<220> FEATURE:
<223> OTHER INFORMATION: Primer F:430

<400> SEQUENCE: 24
atgacctccc agctggagtg catgacctgg                                        30

<210> SEQ ID NO 25
<211> LENGTH: 30
<212> TYPE: DNA
<213> ORGANISM: Artificial Sequence
<220> FEATURE:
<223> OTHER INFORMATION: Primer F:440

<400> SEQUENCE: 25
atgacctccc agctggagtg ctacacctgg                                        30

<210> SEQ ID NO 26
<211> LENGTH: 32
<212> TYPE: DNA
<213> ORGANISM: Artificial Sequence
<220> FEATURE:
<223> OTHER INFORMATION: Primer R: 430, 440

<400> SEQUENCE: 26
ccagctgcca gaagaagttc gcccgcagcg ac                                     32
```

CANCER THERAPY UTILIZING COMBINATION OF ORAL TUMOR VACCINE AND IMMUNOSUPPRESSION INHIBITOR

TECHNICAL FIELD

The present invention relates to an anti-tumor agent including a transformed *Bifidobacterium* capable of expressing and displaying a WT1 protein as an antigen, for use in combination with an immunosuppression inhibitor.

The present application is a National Stage Application of PCT/JP2017/044123, filed Dec. 8, 2017, which claims priority from Japanese Patent Application No. 2016-250560, which is incorporated herein by reference.

BACKGROUND ART

The Wilms tumor 1 (WT1) gene is a gene isolated as a gene responsible for Wilms tumor, which is a pediatric renal tumor. In Wilms tumor, deletion or mutation of the gene is found, and transfer of a normal WT1 gene into a cell line derived from Wilms tumor inhibits cell growth. Accordingly, the WT1 gene has been considered to be a tumor suppressor gene. However, a later investigation has confirmed that a WT1 protein is highly expressed in leukemia and various types of solid cancers, and the WT1 gene is considered to serve a function of an oncogene rather than a tumor suppressor gene (Non Patent Literature 1: Jpn J Clin Oncol 2010; 40: 377-387). Of the solid cancers, for example, prostate cancer has been reported to express the WT1 gene in about 50% of clinical tumor samples (Non Patent Literature 2: Modern Pathology 2006; 19: 804-814).

Cancer immunotherapy started with LAK therapy based on innate immunity in the 1980s, and there have been performed: innate immunotherapy, such as NK cell therapy; and treatment involving utilizing acquired immunity, such as peptide therapy involving targeting a peptide constituting a fragment of a protein serving as a cancer antigen, or dendritic cell vaccine therapy involving causing dendritic cells to recognize a cancer peptide and returning the cells into the body.

It has been confirmed that, when a mouse is immunized with a WT1 peptide, or when dendritic cells differentiated from human peripheral blood mononuclear cells are stimulated with a WT1 peptide, the WT1 peptide can be utilized as a dendritic cell vaccine capable of inducing WT1-specific cytotoxic T cells (CTLs). In addition, progress has also been made in clinical testing involving using the WT1 peptide. The related-art WT1 peptide is generated so as to be adapted to a certain human leukocyte antigen (HLA), and hence it has been necessary to identify an HLA allele of a patient by DNA typing (Patent Literature 1: JP 5714619 B2). In a later investigation, treatment of cancer using a complete sequence-type vaccine covering a complete sequence of the WT1 protein has been attempted. The vaccine is also applicable to patients of various HLA types. The vaccine also activates cancer antigen-specific killer T cells and helper T cells that promote immune responses.

The most general administration route of the WT1 vaccine is subcutaneous or intradermal injection, but attempts have also been made to induce immunity by various administration routes other than the above-mentioned route, for example, transdermal administration and mucosal administration, such as buccal administration, nasal administration, and sublingual administration. However, no report has heretofore been made on oral administration.

A cell membrane is a biological membrane that separates the inside of a cell from the outside. On a surface of the cell membrane, there are a large number of membrane proteins each having a function of providing information on the cell or a function of transporting a substance endogenous or exogenous to the cell. The following concept has been proposed: a certain antigen is fused to a membrane protein so as to be displayed on a cell surface of a microorganism and be used as an oral vaccine for artificially inducing an antigen-antibody reaction. For example, there is known an example in which a vector having a gene encoding a membrane-binding portion of an enzyme protein, such as poly-γ-glutamate synthetase, is utilized to display a target protein on a cell surface of a host microorganism (Patent Literature 2: JP 2005-50054 A). In addition, with regard to a technology involving using, as a vaccine, a flagellin protein derived from a bacterium that causes an infectious disease, there is a report on an oral vaccine containing, as a capsule content, a transformed microorganism expressing flagellin (Patent Literature 3: JP 5187642 B2). In Patent Literature 3, it is reported that the transformed microorganism is prepared using, as the bacterium to be caused to produce flagellin, any of intestinal bacteria that are commonly referred to as good bacteria, such as microorganisms belonging to the genus *Bifidobacterium* (which are collectively referred to as "*Bifidobacterium*") or lactic acid bacteria.

The *Bifidobacterium* is an indigenous bacterium found downstream in the small intestine of a human or other animals, or in the large intestine thereof. The *Bifidobacterium* is an obligately anaerobic Gram-positive bacterium, and hence has high selectivity in culture. Besides, the *Bifidobacterium* has high biocompatibility and does not have endotoxins, which are found in Gram-negative bacteria, and hence the *Bifidobacterium* is highly safe. Therefore, the *Bifidobacterium* has been GRAS-approved according to a standard of a review system regarding food safety. In addition, there is a report that the *Bifidobacterium* has a property of binding to mucus formed of mucin with which the intestinal tract is covered. Accordingly, the *Bifidobacterium* is considered to have a higher property of adhering to the intestinal wall than those of other bacteria in the intestines. There have already been developed and reported a technology for expressing and displaying a protein or a peptide on a surface of such *Bifidobacterium*, and a technology concerning a novel vaccine based on the *Bifidobacterium*, which uses the above-mentioned technology (Patent Literature 4: JP 5561681 B2).

In recent years, as the cancer immunotherapy, utilization of immune checkpoint inhibitors (CPIs), which are immunosuppression inhibitors, has been attracting attention. A combination of a cancer vaccine and the immune checkpoint inhibitor has been tested, but there are still few clinical reports thereon (Non Patent Literature 3: Vaccines 2016, 4(4), 37). The cancer vaccine is available in various forms, such as peptides, DNA, and cells. However, there is no report on combined use of the WT1 protein serving as an antigen with the immune checkpoint inhibitor, and there is also no report on combined use of the oral vaccine with the immune checkpoint inhibitor.

CITATION LIST

Non Patent Literature

[NPL 1] Jpn J Clin Oncol 2010; 40: 377-387
[NPL 2] Modern Pathology 2006; 19: 804-814
[NPL 3] Vaccines 2016, 4(4), 37

Patent Literature

[PTL 1] JP 5714619 B2
[PTL 2] JP 2005-500054 A
[PTL 3] JP 5187642 B2
[PTL 4] JP 5561681 B2

SUMMARY OF INVENTION

Technical Problem

An object of the present invention is to provide a combination therapy effective in cancer immunotherapy.

Solution to Problem

The inventors of the present invention have made extensive investigations, and as a result, have found that an anti-tumor effect is boosted by using a transformed *Bifidobacterium* capable of expressing and displaying a WT1 protein in combination with an immunosuppression inhibitor. Thus, the inventors have completed the present invention.

That is, the present invention includes the following.

1. An anti-tumor agent, including a transformed *Bifidobacterium* containing:

DNA encoding a WT1 protein; and

DNA encoding a GNB/LNB substrate-binding membrane protein derived from a *Bifidobacterium*, the transformed *Bifidobacterium* being designed to express and display the WT1 protein as an antigen on a surface of the transformed *Bifidobacterium*, the anti-tumor agent being for use in combination with an immunosuppression inhibitor.

2. The anti-tumor agent according to the above-mentioned item 1, wherein the anti-tumor agent includes a therapeutic agent for solid cancer.

3. The anti-tumor agent according to the above-mentioned item 1 or 2, wherein the anti-tumor agent includes a therapeutic agent for prostate cancer.

4. The anti-tumor agent according to any one of the above-mentioned items 1 to 3, wherein the immunosuppression inhibitor includes an immune checkpoint inhibitor, and includes at least one antibody selected from the group consisting of an anti-PD1 antibody, an anti-PD-L1 antibody, and an anti-CTLA4 antibody.

5. The anti-tumor agent according to any one of the above-mentioned items 1 to 4, wherein the immunosuppression inhibitor includes an anti-PD1 antibody.

6. The anti-tumor agent according to any one of the above-mentioned items 1 to 5, wherein the WT1 protein is expressed and displayed on a cell surface of the transformed *Bifidobacterium* as a fusion protein of the WT1 protein and the GNB/LNB substrate-binding membrane protein (GLBP-WT1 fusion protein).

7. The anti-tumor agent according to any one of the above-mentioned items 1 to 6, wherein the WT1 protein to be expressed and displayed on a cell surface of the transformed *Bifidobacterium* includes any one of the following items 1) to 3):

1) a protein identified by an amino acid sequence identified by SEQ ID NO: 1;

2) a protein identified based on an amino acid sequence having one or two or more amino acids substituted, deleted, added, or introduced in the amino acid sequence identified by SEQ ID NO: 1, the protein having immunogenicity as a vaccine; and 3) a protein identified based on an amino acid sequence having 60% or more homology to the amino acid sequence identified by SEQ ID NO: 1, the protein having immunogenicity as a vaccine.

8. The anti-tumor agent according to any one of the above-mentioned items 1 to 7, wherein the DNA encoding the WT1 protein to be expressed and displayed on a cell surface of the transformed *Bifidobacterium* includes any one of the following items 1) to 4):

1) DNA having a base sequence identified by SEQ ID NO: 2;

2) DNA encoding a protein obtained based on amino acid sequence information identified by SEQ ID NO: 1;

3) DNA capable of hybridizing under stringent conditions with DNA having a base sequence identified by the item 1) or 2); and 4) DNA having a base sequence having 60% or more homology to a base sequence identified by any one of the items 1) to 3).

9. The anti-tumor agent according to any one of the above-mentioned items 1 to 8, wherein the WT1 protein to be expressed and displayed on a cell surface of the transformed *Bifidobacterium* includes a protein identified by an amino acid sequence identified by SEQ ID NO: 14 or SEQ ID NO: 16.

10. The anti-tumor agent according to any one of the above-mentioned items 1 to 9, wherein the transformed *Bifidobacterium* further contains DNA encoding a protein having an adjuvant function between the DNA encoding a WT1 protein and the DNA encoding a GNB/LNB substrate-binding membrane protein derived from a *Bifidobacterium*.

11. The anti-tumor agent according to any one of the above-mentioned items 1 to 10, wherein the transformed *Bifidobacterium* serves as an active ingredient of a tumor vaccine formulation.

12. The anti-tumor agent according to the above-mentioned item 11, wherein the tumor vaccine formulation includes an oral formulation.

13. A method of preventing or treating a cancer, including using a transformed *Bifidobacterium* designed to express and display a WT1 protein as an antigen on a surface of the transformed *Bifidobacterium* in combination with an immunosuppression inhibitor.

14. The method of preventing or treating a cancer according to the above-mentioned item 13, wherein the cancer includes a cancer capable of highly expressing the WT1 protein.

15. The method of preventing or treating a cancer according to the above-mentioned item 13, wherein the cancer includes one kind or a plurality of cancers selected from prostate cancer, lung cancer, bladder cancer, stomach cancer, colorectal cancer, breast cancer, germ cell cancer, liver cancer, skin cancer, uterine cancer, cervical cancer, ovarian cancer, brain cancer, esophageal cancer, malignant mesothelioma, renal cancer, leukemia, myelodysplastic syndrome, multiple myeloma, and malignant lymphoma.

16. The method of preventing or treating a cancer according to the above-mentioned item 15, wherein the cancer includes prostate cancer.

Advantageous Effects of Invention

The combined use of the transformed *Bifidobacterium* designed to express and display the WT1 protein as an antigen on the surface of the *Bifidobacterium* of the present invention with the immunosuppression inhibitor can exhibit an excellent anti-tumor effect as compared to the transformed *Bifidobacterium* alone and the immunosuppression inhibitor alone. For example, in prostate cancer, an excellent anti-tumor effect is confirmed even when the transformed *Bifidobacterium* is administered alone, but the anti-tumor effect can be further boosted through the combined use with the immunosuppression inhibitor.

The transformed *Bifidobacterium* in the present invention can express and display the WT1 protein on the cell surface of the *Bifidobacterium*, and can be utilized for a tumor expressing the WT1 protein. When used as an oral vaccine formulation, the transformed *Bifidobacterium* in the present invention is easy to ingest even for a child or an elderly person, and besides, is free of pain involved in vaccine inoculation by general injection. In particular, the transformed *Bifidobacterium* of the present invention is highly safe by virtue of the use of the *Bifidobacterium*, which has an experience in food. The combined use of the present invention can be expected to achieve a high anti-tumor effect while minimizing a burden on a patient, and is convenient because the setting of an administration schedule and the like can be performed flexibly.

In addition, the transformed *Bifidobacterium* of the present invention is the *Bifidobacterium* capable of expressing and displaying a protein covering a nearly complete sequence of a WT1 protein, and hence has low HLA restriction, unlike a WT1 peptide vaccine restricted to a certain HLA. Accordingly, the combination therapy of the present invention is applicable to patients of various HLA types.

DESCRIPTION OF EMBODIMENTS

Figure 1:
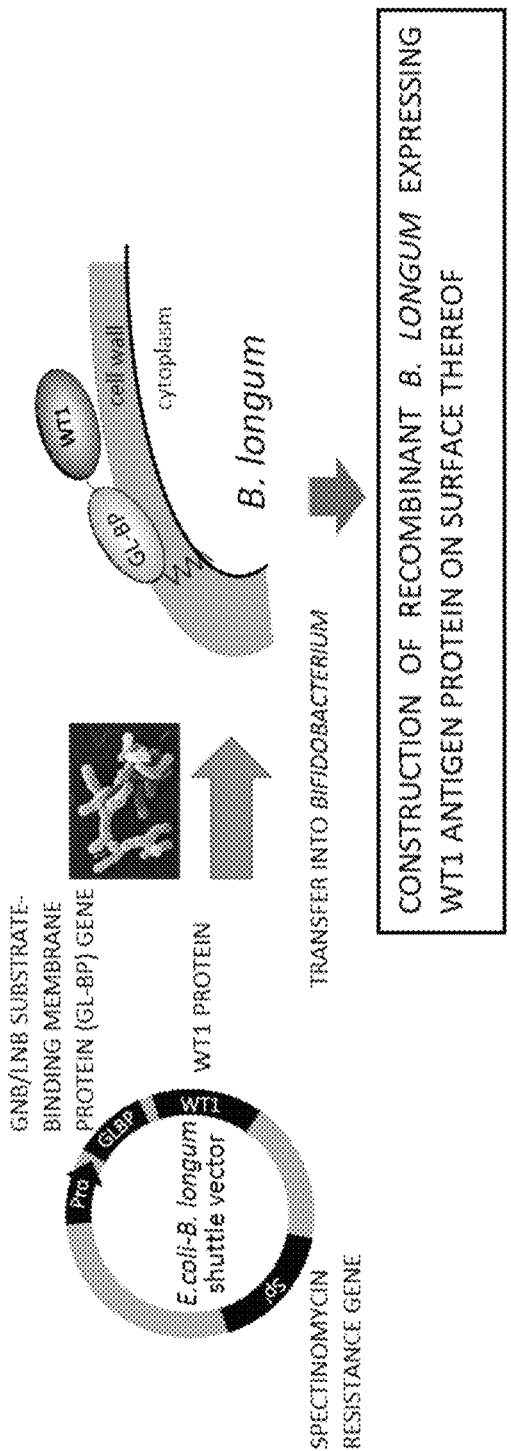
FIG. 1 is a conceptual diagram for illustrating a shuttle vector having a WT1 gene downstream of a GL-BP gene, and a GL-BP-WT1 fusion protein expressed on the surface of a *Bifidobacterium* (Example 1).

The present invention relates to an anti-tumor agent, including a transformed *Bifidobacterium* designed to express and display the WT1 protein as an antigen, the anti-tumor agent being for use in combination with an immunosuppression inhibitor. The immunosuppression inhibitor is a drug capable of inhibiting immunosuppression due to cancer cells, and is used for allowing cancer-specific T cells to be able to function more normally. The present invention provides a combination therapy involving using the transformed *Bifidobacterium* and the immunosuppression inhibitor in combination in cancer treatment. The transformed *Bifidobacterium* designed to express and display a WT1 protein as an antigen and the immunosuppression inhibitor are described in detail below.

I. Transformed *Bifidobacterium* Designed to Express and Display WT1 Protein as Antigen A transformed *Bifidobacterium* of the present invention is designed to express and display a WT1 protein as an antigen on a surface of the *Bifidobacterium* by containing: DNA encoding a WT1 protein; and DNA encoding a GNB/LNB substrate-binding membrane protein derived from a *Bifidobacterium*.

(WT1 Protein)

A WT1 protein is a protein encoded by a WT1 gene, which has been isolated as a gene responsible for Wilms tumor, which is a pediatric renal tumor. The WT1 protein has been confirmed to have a plurality of T cell epitopes for various HLA types. A WT1 protein of the present invention only needs to contain at least two or more (preferably three or more, more preferably four or more) T cell epitopes, and may be a full-length protein or may be a partial peptide having a deletion at its N-terminus or C-terminus. The full length of the WT1 protein is exemplified below.

```
Full length of WT1 protein GenBank Accession No.
P22561.1 (SEQ ID NO: 22):
MGSDVRDLNALLPAVSSLGGGGGCGLPVSGARQWAPVLDFAPPGASA

YGSLGGPAPPPAPPPPPPPPHSFIKQEPSWGGAEPHEEQCLSAFTLHF

SGQFTGTAGACRYGPFGPPPPSQASSGQARMFPNAPYLPSCLESQPTI

RNQGYSTVTFDGAPSYGHTPSHHAAQFPNHSFKHEDPMGQQGSLGEQQ

YSVPPPVYGCHTPTDSCTGSQALLLRTPYSSDNLYQMTSQLECMTWNQ

MNLGATLKGMAAGSSSSVKWTEGQSNHGIGYESENHTAPILCGAQYRI

HTHGVFRGIQDVRRVSGVAPTLVRSASETSEKRPFMCAYPGCNKRYFK

LSHLQMHSRKHTGEKPYQCDFKDCERRFSRSDQLKRHQRRHTGVKPFQ

CKTCQRKFSRSDHLKTHTRTHTGKTSEKPFSCRWHSCQKKFARSDELV

RHHNMHQRNMTKLHVAL

Full length of WT1 protein GenBank Accession No.
P19544.2 (SEQ ID NO: 23):
MGSDVRDLNALLPAVPSLGGGGGCALPVSGAAQWAPVLDFAPPGASAY

GSLGGPAPPPAPPPPPPPPHSFIKQEPSWGGAEPHEEQCLSAFTVHF

SGQFTGTAGACRYGPFGPPPPSQASSGQARMFPNAPYLPSCLESQPAI

RNQGYSTVTFDGTPSYGHTPSHHAAQFPNHSFKHEDPMGQQGSLGEQQ

YSVPPPVYGCHTPTDSCTGSQALLLRTPYSSDNLYQMTSQLECMTWNQ

MNLGATLKGVAAGSSSSVKWTEGQSNHSTGYESDNHTTPILCGAQYRI

HTHGVFRGIQDVRRVPGVAPTLVRSASETSEKRPFMCAYPGCNKRYFK

LSHLQMHSRKHTGEKPYQCDFKDCERRFSRSDQLKRHQRRHTGVKPFQ

CKTCQRKFSRSDHLKTHTRTHTGKTSEKPFSCRWPSCQKKFARSDELV

RHHNMHQRNMTKLQLAL
```

Herein, the WT1 protein, which serves as an antigen that may be expressed and displayed on a *Bifidobacterium* is identified by any one of the following items:

1) a protein identified by an amino acid sequence identified by SEQ ID NO: 1;

2) a protein identified based on an amino acid sequence having one or two or more, for example, one to one hundred twenty, preferably one to sixty, one to fifty, one to forty, one to thirty, or one to twenty, more preferably one to ten, still more preferably one to nine amino acids substituted, deleted, added, or introduced in the amino acid sequence identified by SEQ ID NO: 1, the protein having immunogenicity as a vaccine; and 3) a protein identified based on an amino acid sequence having 60% or more, preferably 80% or more, more preferably 90% or more, still more preferably 95% or more, even still more preferably 97% or more, most preferably 98% or more homology to the amino acid sequence identified by SEQ ID NO: 1, the protein having immunogenicity as a vaccine.

```
WT1 protein (SEQ ID NO: 1):
PSQASSGQARMFPNAPYLPSCLESQPTIRNQGYSTVTFDGAPSYGHTP

SHHAAQFPNHSFKHEDPMGQQGSLGEQQYSVPPPVYGCHTPTDSCTGS

QALLLRTPYSSDNLYQMTSQLECMTWNQMNLGATLKGMAAGSSSSVKW

TEGQSNHGIGYESENHTAPILCGAQYRIHTHGVFRGIQDVRRVSGVAP

TLVRSASETSEKRPFMCAYPGCNKRYFKLSHLQMHSRKHTGEKPYQCD

FKDCERRFSRSDQLKRHQRRHTGVKPFQCKTCQRKFSRSDHLKTHTRT

HTGKTSEKPFSCRWHSCQKKFARSDELVRHHNMHQ
```

T cell epitopes contained in the above-mentioned WT1 protein (SEQ ID NO: 1) are shown in Table 1 below. The WT1 protein of the present invention preferably contains two or more of T cell epitopes corresponding to np332, np126, np187, and np235 shown in Table 1. The WT1 protein contains more preferably three or more, still more preferably all four of the T cell epitopes. Each of those T cell epitopes only needs to be capable of inducing a cellular immune response by being recognized by a T cell, and may have an amino acid sequence having one or two or more, for example, one to five, preferably one to three, more preferably one or two, most preferably one amino acid substituted, deleted, added, or introduced in the amino acid sequence.

TABLE 1

| T cell epitope | Peptide | Amino acid | Sequence | HLA restriction |
|---|---|---|---|---|
| CD4 | np332 | a.a. 332-347 | KRYFKLSHLQMHSRKH (SEQ ID NO: 18) | DRB1*0405 |
| CD8 | np126 | a.a. 126-134 | RMFPNAPYL (SEQ ID NO: 19) | A0201 |
|  | np187 | a.a. 187-195 | SLGEQQYSV (SEQ ID NO: 20) | A0201 |
|  | np235 | a.a. 235-243 | CMTWNQMNL (SEQ ID NO: 21) | A2402 |

In addition, the WT1 protein as used herein may be a WT1 protein identified by the following SEQ ID NO: 14.

```
WT1 protein (SEQ ID NO: 14):
PSQASSGQARMFPNAPYLPSCLESQPAIRNQGYSTVTFDGTPSYGHTP

SHHAAQFPNHSFKHEDPMGQQGSLGEQQYSVPPPVYGCHTPTDSCTGS

QALLLRTPYSSDNLYQMTSQLECMTWNQMNLGATLKGVAAGSSSSVKW

TEGQSNHSTGYESDNHTTPILCGAQYRIHTHGVFRGIQDVRRVPGVAP
```

```
TLVRSASETSEKRPFMCAYPGCNKRYFKLSHLQMHSRKHTGEKPYQCD

FKDCERRFSRSDQLKRHQRRHTGVKPFQCKTCQRKFSRSDHLKTHTRT

HTGKTSEKPFSCRWPSCQKKFARSDELVRHHNMHQ
```

In addition, a mutant WT1 protein having an amino acid sequence having a M236Y substitution introduced in an HLA-A*2402-restrictive CTL epitope in the above-mentioned WT1 protein (SEQ ID NO: 14) is shown below. The WT1 protein as used herein may be the following mutant WT1 protein.

```
Mutant WT1 protein (SEQ ID NO: 16):
PSQASSGQARMFPNAPYLPSCLESQPAIRNQGYSTVTFDGTPSYGHTP

SHHAAQFPNHSFKHEDPMGQQGSLGEQQYSVPPPVYGCHTPTDSCTGS

QALLLRTPYSSDNLYQMTSQLECYTWNQMNLGATLKGVAAGSSSSVKW

TEGQSNHSTGYESDNHTTPILCGAQYRIHTHGVFRGIQDVRRVPGVAP

TLVRSASETSEKRPFMCAYPGCNKRYFKLSHLQMHSRKHTGEKPYQCD

FKDCERRFSRSDQLKRHQRRHTGVKPFQCKTCQRKFSRSDHLKTHTRT

HTGKTSEKPFSCRWPSCQKKFARSDELVRHHNMHQ
```

The WT1 protein as used herein encompasses an engineered WT1 protein as well. Herein, the engineered WT1 protein refers to a protein obtained by engineering all or part of the amino acids of the WT1 protein identified above through substitution, modification, or the like. The engineered WT1 protein includes a protein having an amino acid sequence having all or part of amino acids, for example, one or two or more, for example, one, two, three, four, five, six, seven, eight, nine, ten, eleven, or twelve amino acids modified in the amino acid sequence identified by the above-mentioned items 1) to 3). Examples of the "modification" of the amino acid that may be present in the engineered WT1 protein include, but not limited to, acetylation, alkylation, such as methylation, glycosylation, hydroxylation, carboxylation, aldehydation, phosphorylation, sulfonylation, formylation, fatty chain addition modification, such as myristoylation, palmitoylation, or stearoylation, octanoylation, esterification, amidation, deamidation, disulfide bond formation modification, such as cystine modification, glutathione modification, or thioglycolic acid modification, glycation, ubiquitination, succinimide formation, glutamylation, and prenylation. The engineered WT1 protein may contain one or more amino acid substitutions, deletions, or additions in combination with one or more amino acid modifications.

(*Bifidobacterium*)

The "*Bifidobacterium*" as used herein refers to a microorganism belonging to the genus *Bifidobacterium*. Examples of the *Bifidobacterium* include *Bifidobacterium adolescentis*, *Bifidobacterium angulatum* (*B. angulatum*), *Bifidobacterium animalis* subsp. *animalis* (*B. animalis* subsp. *animalis*), *Bifidobacterium animalis* subsp. *lactis* (*B. animalis* subsp. *lactis*), *Bifidobacterium asteroides* (*B. asteroides*), *Bifidobacterium bifidum* (*B. bifidum*), *Bifidobacterium boum* (*B. boum*), *Bifidobacterium breve* (*B. breve*), *Bifidobacterium catenulatum* (*B. catenulatum*), *Bifidobacterium choerinum* (*B. choerinum*), *Bifidobacterium coryneforme* (*B. coryneforme*), *Bifidobacterium cuniculi* (*B. cuniculi*), *Bifidobacterium denticolens* (*B. denticolens*), *Bifidobacterium dentium* (*B. dentium*), *Bifidobacterium gallicum* (*B. gallicum*), *Bifidobacterium gallinarum* (*B. gallinarum*), *Bifidobacterium globosum* (*B. globosum*), *Bifidobacterium indicum* (*B. indicum*), *Bifidobacterium infantis* (*B. infantis*), *Bifidobacterium inopinatum* (*B. inopinatum*), *Bifidobacterium lactis* (*B. lactis*), *Bifidobacterium longum* (*B. longum*), *Bifidobacterium magnum* (*B. magnum*), *Bifidobacterium merycicum* (*B. merycicum*), *Bifidobacterium minimum* (*B. minimum*), *Bifidobacterium parvulorum* (*B. parvulorum*), *Bifidobacterium pseudocatenulatum* (*B. pseudocatenulatum*), *Bifidobacterium pseudolongum* subsp. *globosum* (*B. pseudolongum* subsp. *globosum*), *Bifidobacterium pseudolongum* subsp. *pseudolongum* (*B. pseudolongum* subsp. *pseudolongum*), *Bifidobacterium pullorum* (*B. pullorum*), *Bifidobacterium ruminale* (*B. ruminale*), *Bifidobacterium ruminantium* (*B. ruminantium*), *Bifidobacterium saeculare* (*B. saeculare*), *Bifidobacterium scardovii* (*B. scardovii*), *Bifidobacterium subtile* (*B. subtile*), *Bifidobacterium suis* (*B. suis*), *Bifidobacterium thermacidophilum* (*B. thermacidophilum*), and *Bifidobacterium thermophilum* (*B. thermophilum*).

Of those, *Bifidobacterium adolescentis*, *Bifidobacterium animalis* subsp. *animalis* (*B. animalis* subsp. *animalis*), *Bifidobacterium animalis* subsp. *lactis* (*B. animalis* subsp. *lactis*), *Bifidobacterium bifidum* (*B. bifidum*), *Bifidobacterium breve* (*B. breve*), *Bifidobacterium lactis* (*B. lactis*), *Bifidobacterium longum* (*B. longum*), and *Bifidobacterium pseudolongum* subsp. *pseudolongum* (*B. pseudolongum* subsp. *pseudolongum*) are preferably used.

In addition, their resistant strains or mutant strains may be used. Those strains are commercially available or easily available from the depository institution or the like. There are given, for example, *B. longum* JCM1217 (ATCC15707) and *B. bifidum* ATCC11863.

(GNB/LNB Substrate-Binding Membrane Protein)

A GNB/LNB substrate-binding membrane protein (GL-BP: galacto-n-biose-lacto-n-biose I-binding protein) is a membrane protein belonging to the ATP binding cassette protein (ABC protein) family, which transports lacto-N-biose (i.e., N-acetyl-3-O-β-D-galactopyranosyl-D-glucosamine) and galacto-N-biose (i.e., N-acetyl-3-O-(β-D-galactopyranosyl)-α-D-galactosamine) of the *Bifidobacterium*. The GNB/LNB substrate-binding membrane protein is hereinafter sometimes referred to simply as "GL-BP". ABC proteins are important membrane proteins that actively transport specific substances on the cell membranes of all organisms through the use of adenosine triphosphate (ATP) as energy, and many kinds of ABC proteins are present on the cell membranes. Accordingly, the GL-BP, which is a kind of ABC protein, is ubiquitously expressed through the utilization of an appropriate promoter in a *Bifidobacterium* having a cellular function for expressing the GL-BP on the surface thereof. Herein, the structure of the GL-BP is not limited to naturally occurring GL-BP, and the GL-BP may have one or more of substitutions, insertions, or deletions in its constituent amino acids as long as the GL-BP has an ability to be expressed on the cell surface of the *Bifidobacterium*.

(Fusion Protein to be Displayed on Surface of *Bifidobacterium*)

In the present invention, the WT1 protein to be expressed and displayed on the surface of the *Bifidobacterium* is expressed as a fusion protein with the GL-BP. In the fusion protein, the GL-BP and the WT1 protein are linked in the stated order from the N-terminus. As necessary, the fusion protein may include a protein having an adjuvant function between the GL-BP and the WT1 protein.

(Preparation of Transformed *Bifidobacterium*)

A procedure for preparing the transformed *Bifidobacterium* capable of expressing and displaying the WT1 protein as an antigen is described in order of operations.

1. Acquisition of DNA Encoding Each Protein

DNA encoding the GL-BP and DNA encoding the WT1 protein may be obtained on the basis of respective known gene information or amino acid sequence information. For example, the DNAs may be acquired by amplifying, through a polymerase chain reaction (PCR), genomic DNA or cDNA prepared from any *Bifidobacterium* serving as a template with the use of a primer pair generated on the basis of genomic information on a structural gene for the GL-BP of the *Bifidobacterium*. In general, a plurality of kinds of genetic codes exist for one amino acid, and hence a gene having a base sequence different from a known base sequence or from a base sequence based on a known amino acid sequence may be adopted. DNA encoding the GL-BP of *B. longum* may be obtained on the basis of, for example, gene information on the GL-BP of *B. longum* identified in Acta Crystallographica Section F., 2007, Volume F63, p. 751. The DNA encoding the GL-BP of *B. longum* may be obtained by amplifying, through PCR, chromosomal DNA or cDNA of *B. longum* serving as a template with the use of a primer pair generated on the basis of gene information. The DNA encoding the WT1 protein may be generated and obtained by a method known per se or any method to be developed in the future on the basis of the amino acid sequence information identified for any of the above-mentioned WT1 proteins. DNAs encoding proteins other than the above-mentioned WT1 proteins may be similarly generated and obtained by a method known per se or any method to be developed in the future.

The DNA encoding each protein described above may be DNA capable of hybridizing under stringent conditions with the DNA acquired as described above. The DNA capable of hybridizing under stringent conditions means DNA obtained by a colony hybridization method, a plaque hybridization method, a Southern blot hybridization method, or the like through the use of the above-mentioned DNA as a probe. A specific example thereof is DNA that can be identified by: performing hybridization at about 65° C. in the presence of sodium chloride at from about 0.7 M to about 1.0 M with a filter having immobilized thereon DNA derived from a colony or a plaque; and then washing the filter with an SSC solution having a concentration of from about 0.1× to about 2× (the composition of an SSC solution having a concentration of 1× is formed of 150 mM sodium chloride and 15 mM sodium citrate) under the condition of about 65° C. A specific example of the DNA capable of hybridizing is DNA having at least about 80% or more homology to the base sequence of the above-mentioned DNA encoding each protein obtained on the basis of known base sequence information or amino acid sequence information, preferably DNA having about 90% or more homology thereto, still more preferably DNA having about 95% or more homology thereto. DNA encoding each protein obtained on the basis of amino acid sequence information may have a different codon as long as an amino acid is encoded.

More specifically, the DNA encoding the WT1 protein is identified by any one of the following items:

1) DNA having a base sequence identified by SEQ ID NO: 2;
2) DNA encoding a protein obtained based on amino acid sequence information identified by SEQ ID NO: 1;
3) DNA capable of hybridizing under stringent conditions with DNA having a base sequence identified by the item 1) or 2); and
4) DNA having a base sequence having 60% or more, preferably 80% or more homology to a base sequence identified by any one of the items 1) to 3).

```
DNA encoding WT1 protein
                                            (SEQ ID NO: 2)
CTCGAGCCGTCCCAGGCGTCGTCGGGCCAGGCGAGGATGTTCCCGAAC

GCGCCCTACCTGCCCAGCTGCCTGGAGTCCCAGCCGACGATCCGCAAC

CAGGGCTACTCCACCGTGACGTTCGACGGCGCCCGTCCTACGGCCAC

ACGCCCAGCCACCACGCCGCCCAGTTCCCGAACCACAGCTTCAAGCAC

GAAGACCCCATGGGCCAGCAGGGCAGCCTCGGCGAACAGCAGTACAGC

GTGCCGCCGCCGGTCTACGGCTGCCACACCCCGACCGACTCCTGCACG

GGCTCCCAGGCCCTGCTCCTGCGTACGCCGTACTCCTCCGACAACCTC

TACCAGATGACCTCCCAGCTGGAGTGCATGACCTGGAACCAGATGAAC

CTGGGCGCCACGCTGAAGGGAATGGCCGCGGGGTCGTCGAGCTCCGTC

AAGTGGACCGAAGGCCAGTCCAACCACGGCATCGGCTACGAGTCCGAG

AACCACACCGCGCCGATCCTGTGCGGAGCCCAGTACCGCATCCACACG

CACGGCGTCTTCCGCGGCATCCAGGACGTCCGGCGCGTCTCCGGCGTC

GCGCCGACCCTGGTGCGGTCCGCCTCCGAGACCTCCGAGAAGCGCCCG

TTCATGTGCGCCTACCCGGGCTGCAACAAGCGCTACTTCAAGCTCTCG

CACCTGCAGATGCACTCCCGGAAGCACACCGGCGAGAAGCCGTACCAG

TGCGACTTCAAGGACTGCGAACGCCGCTTCTCGCGCAGCGACCAGCTG

AAGCGCCACCAGCGTAGGCACACCGGCGTGAAGCCCTTCCAGTGCAAG

ACCTGCCAGCGCAAGTTCTCCCGCAGCGACCACCTCAAGACGCACACC

CGCACCCACACCGGCAAGACGTCCGAGAAGCCGTTCTCGTGCCGCTGG

CACAGCTGCCAGAAGAAGTTCGCCCGCAGCGACGAGCTCGTGCGCCAC

CACAACATGCACCAGTGAAGCATGC
```

In addition, the DNA encoding the WT1 protein is, for example, DNA having a base sequence identified by the following SEQ ID NO: 15 or SEQ ID NO: 17.

```
DNA encoding WT1 protein
                                           (SEQ ID NO: 15)
CCGTCCCAGGCGTCGTCGGGCCAGGCGAGGATGTTCCCGAACGCGCCC

TACCTGCCCAGCTGCCTGGAGTCCCAGCCGGCGATCCGCAACCAGGGC

TACTCCACCGTGACGTTCGACGGCACCCCGTCCTACGGCCACACGCCC

AGCCACCACGCCGCCCAGTTCCCGAACCACAGCTTCAAGCACGAAGAC

CCCATGGGCCAGCAGGGCAGCCTCGGCGAACAGCAGTACAGCGTGCCG

CCGCCGGTCTACGGCTGCCACACCCCGACCGACTCCTGCACGGGCTCC

CAGGCCCTGCTCCTGCGTACGCCGTACTCCTCCGACAACCTCTACCAG

ATGACCTCCCAGCTGGAGTGCATGACCTGGAACCAGATGAACCTGGGC

GCCACGCTGAAGGGAGTCGCCGCGGGGTCGTCGAGCTCCGTCAAGTGG

ACCGAAGGCCAGTCCAACCACTCCACCGGCTACGAGTCCGACAACCAC
```

-continued
ACCACGCCGATCCTGTGCGGAGCCCAGTACCGCATCCACACGCACGGC

GTCTTCCGCGGCATCCAGGACGTCCGGCGCGTCCCCGGCGTCGCGCCG

ACCCTGGTGCGGTCCGCCTCCGAGACCTCCGAGAAGCGCCCGTTCATG

TGCGCCTACCCGGGCTGCAACAAGCGCTACTTCAAGCTCTCGCACCTG

CAGATGCACTCCCGGAAGCACACCGGCGAGAAGCCGTACCAGTGCGAC

TTCAAGGACTGCGAACGCCGCTTCTCGCGCAGCGACCAGCTGAAGCGC

CACCAGCGTAGGCACACCGGCGTGAAGCCCITCCAGTGCAAGACCTGC

CAGCGCAAGTTCTCCCGCAGCGACCACCTCAAGACGCACACCCGCACC

CACACCGGCAAGACGTCCGAGAAGCCGTTCTCGTGCCGCTGGCCCAGC

TGCCAGAAGAAGTTCGCCCGCAGCGACGAGCTCGTGCGCCACCACAAC

ATGCACCAGTGAA

DNA encoding WT1 protein
(SEQ ID NO: 17)
CCGTCCCAGGCGTCGTCGGGCCAGGCGAGGATGTTCCCGAACGCGCCC

TACCTGCCCAGCTGCCTGGAGTCCCAGCCGGCGATCCGCAACCAGGGC

TACTCCACCGTGACGTTCGACGGCACCCCGTCCTACGGCCACACGCCC

AGCCACCACGCCGCCCAGTTCCCGAACCACAGCTTCAAGCACGAAGAC

CCCATGGGCCAGCAGGGCAGCCTCGGCGAACAGCAGTACAGCGTGCCG

CCGCCGGTCTACGGCTGCCACACCCCGACCGACTCCTGCACGGGCTCC

CAGGCCCTGCTCCTGCGTACGCCGTACTCCTCCGACAACCTCTACCAG

ATGACCTCCCAGCTGGAGTGCTACACCTGGAACCAGATGAACCTGGGC

GCCACGCTGAAGGGAGTCGCCGCGGGGTCGTCGAGCTCCGTCAAGTGG

ACCGAAGGCCAGTCCAACCACTCCACCGGCTACGAGTCCGACAACCAC

ACCACGCCGATCCTGTGCGCGGAGCCCAGTACCGCATCCACACGCACGGC

GTCTTCCGCGGCATCCAGGACGTCCGGCGCGTCCCCGGCGTCGCGCCG

ACCCTGGTGCGGTCCGCCTCCGAGACCTCCGAGAAGCGCCCGTTCATG

TGCGCCTACCCGGGCTGCAACAAGCGCTACTTCAAGCTCTCGCACCTG

CAGATGCACTCCCGGAAGCACACCGGCGAGAAGCCGTACCAGTGCGAC

TTCAAGGACTGCGAACGCCGCTTCTCGCGCAGCGACCAGCTGAAGCGC

CACCAGCGTAGGCACACCGGCGTGAAGCCCTTCCAGTGCAAGACCTGC

CAGCGCAAGTTCTCCCGCAGCGACCACCTCAAGACGCACACCCGCACC

CACACCGGCAAGACGTCCGAGAAGCCGTTCTCGTGCCGCTGGCCCAGC

TGCCAGAAGAAGTTCGCCCGCAGCGACGAGCTCGTGCGCCACCACAAC

ATGCACCAGTGAA

2. Preparation of Vector for Transforming *Bifidobacterium*

The preparation of recombinant DNA having the DNAs encoding the respective proteins prepared in the section 1. is described. Herein, for the recombinant DNA, an expression vector or a chromosomal integration vector (e.g., a homologous recombination vector) may be used. A plasmid to be used for the preparation of such vector is not particularly limited as long as the plasmid can be expressed in the *Bifidobacterium*, and the plasmid may be a plasmid known per se or any plasmid to be developed in the future. For example, as a plasmid derived from the *Bifidobacterium*, there may be used pTB6, pBL67, pBL78, pNAL8H, pNAL8M, pNAC1, pBC1, pMB1, pGBL8b, or the like. A composite plasmid of any of those plasmids and a plasmid of *E. coli* may be used. For example, pBLES100, pKKT427, or pRM2 may be used. From the viewpoints of the stability of expression and the ease of preparation of DNA for the preparation of a transformant, of the above-mentioned plasmids, a composite plasmid synthesized from a plasmid of *B. longum* and a plasmid of *E. coli* is suitable.

From the viewpoint of selecting a transformant, the expression vector suitably has a selectable marker, such as antibiotic resistance or an amino acid requirement, on the basis of a method known per se. The expression vector preferably has added thereto a regulatory sequence in order to express the fusion protein of the GL-BP and the WT1 protein, or so as to be advantageous for the expression. Examples of the regulatory sequence include a promoter sequence, a leader sequence, a propeptide sequence, an enhancer sequence, a signal sequence, and a terminator sequence. The origin of each of those regulatory sequences is not particularly limited as long as the regulatory sequence is expressed in the *Bifidobacterium*. The promoter sequence is not particularly limited as long as the promoter sequence is expressed in the *Bifidobacterium*. From the viewpoint of expression efficiency, the promoter sequence of the histone-like protein (HU) of *B. longum*, the LDH promoter thereof, or the like is preferably used. In addition, from the viewpoint of enhancing expression efficiency, the expression vector preferably has a terminator sequence. As the terminator sequence, the terminator sequence of the HU gene is preferably used. In addition, DNA encoding a linker having an appropriate length may be arranged between the DNA encoding the GL-BP and the DNA encoding the WT1 protein.

A cloning vector is prepared by introducing, as necessary, a regulatory sequence, such as a promoter sequence or a terminator sequence, and a selectable marker gene into the above-mentioned plasmid, as described above. Examples of the selectable marker include: antibiotic resistance markers, such as spectinomycin (SPr), ampicillin (Ampr), tetracycline (TETr), kanamycin (KMr), streptomycin (STr), and neomycin (NEOr); fluorescent markers, such as a green fluorescent protein (GFP) and a red fluorescent protein (REP); and enzymes, such as LacZ. The cloning vector preferably has, for example, a linker having a multiple cloning site downstream of its promoter. Through the use of such linker, the DNA encoding the fusion protein is integrated downstream of the promoter and so as to allow in-frame expression of the fusion protein. As the plasmid for the cloning vector, pBLES100, pBLEM100, or the like may be typically used.

In-frame integration of the acquired HU promoter sequence, DNA encoding the GL-BP, and DNA encoding the WT1 protein into the plasmid pBLES100 can generate a vector for expressing the fusion protein on the surface of the *Bifidobacterium*. The expression vector generated by such method is used for the transformation of the *Bifidobacterium*.

3. Preparation of Transformed *Bifidobacterium* Expressing Fusion Protein

The recombinant DNA, for example, the expression vector is transferred into the *Bifidobacterium* serving as a host. As a transformation method, a method known per se or any method to be developed in the future may be applied. Specific examples thereof include an electroporation method, a calcium phosphate method, a lipofection method, a calcium ion method, a protoplast method, a microinjection method, and a particle gun method. In the present invention, an electroporation method is preferably used. The electroporation method may be performed under the conditions of from 0.5 kV/cm to 20 kV/cm and from 0.5 μsec to 10 msec. The electroporation method is desirably performed under the conditions of more preferably from 2 kV/cm to 10 kV/cm and from 50 μsec to 5 msec.

The transformant may be selected by using the selectable marker of the fusion protein expression vector as an indicator. As a medium for culturing the transformant, there are given media suited for respective host microorganisms, for example, a glucose blood liver (BL) agar medium, a de Man-Rogosa-Sharpe (MRS) agar medium, a Gifu anaerobic medium (GAM) agar medium, an improved GAM (TGAM) agar medium, a Briggs agar medium, and a yeast extract-glucose-peptone (YGP) agar medium.

The transformant is preferably cultured under anaerobic culture conditions under which the *Bifidobacterium* can be cultured. When the culture is performed under anaerobic conditions, the growth of aerobic bacteria can be prevented. The anaerobic conditions are culture in a hermetic vessel capable of keeping anaerobicity that allows the growth of the *Bifidobacterium*, and examples thereof include conditions that can be established in an anaerobic chamber, an anaerobic box, or the like. A culture temperature only needs to be a temperature at which the *Bifidobacterium* can be cultured, and is generally from 4° C. to 45° C., preferably from 15° C. to 40° C., more preferably from 24° C. to 37° C.

The fusion protein expressed and displayed on the surface of the obtained transformed *Bifidobacterium* may be confirmed by a method known per se that is applied in gene recombination technology or any method to be developed in the future. The fusion protein may be confirmed by, for example, a western blotting method. The western blotting method may also be performed by a method known per se. In particular, that the WT1 protein is expressed and displayed on the surface of the *Bifidobacterium* can be easily confirmed by subjecting the transformed *Bifidobacterium* to an immunoantibody method involving using, for example, an antibody against the WT1 protein and an FITC-labeled anti-IgG antibody. In the case of expressing a fusion protein of the GL-BP, a protein having an adjuvant function, and the WT1 protein, the protein having an adjuvant function and the WT1 protein are expressed and displayed on the surface of the *Bifidobacterium*, and hence the antibody to be used for the confirmation may be an antibody against any of the proteins.

The transformed *Bifidobacterium* that has been confirmed to express and display the WT1 protein on the surface thereof may be cultured, recovered, and used as it is for the production of a formulation, by methods to be generally used by a person skilled in the art. The obtained *Bifidobacterium* may be inactivated by heat sterilization treatment, radiation irradiation, or the like before use. The transformed *Bifidobacterium* may be subjected to post-treatment by a known method. For example, partial purification may be performed by centrifugation or the like. In addition, as desired, after the partial purification has been performed, the transformed *Bifidobacterium* may be dissolved or suspended in a solvent that has been conventionally used in the art, such as saline, phosphate-buffered saline (PBS), or lactated Ringer's solution. In addition, as desired, the transformed *Bifidobacterium* may be freeze-dried or spray-dried to be formed into a powdery product or a granular product.

(Formulation Containing Transformed *Bifidobacterium*)

When administered for the purpose of treating or preventing a disease, the transformed *Bifidobacterium* of the present invention having the WT1 protein expressed and displayed thereon may be administered in the form of any formulation. An administration route is not particularly limited, and oral administration or parenteral administration may be performed, but oral administration is suitable.

As a formulation suitable for the oral administration, there are given, for example, a tablet, a granule, a fine granule, a powder, a syrup, a solution, a capsule, and a suspension. As a formulation suitable for the parenteral administration, there are given, for example, an injection, an infusion, an inhalation, a spray, a suppository, a transdermal formulation, and a transmucosal formulation.

In the production of a liquid formulation for the oral administration, there may be used formulation additives, for example: water; sugars, such as sucrose, sorbit, and fructose; glycols, such as polyethylene glycol and propylene glycol; oils, such as sesame oil, olive oil, and soybean oil; and preservatives, such as a p-hydroxybenzoic acid ester. In addition, in the production of a solid formulation, such as a capsule, a tablet, a powder, or a granule, there may be used, for example: excipients, such as lactose, glucose, sucrose, and mannite; disintegrants, such as starch and sodium alginate; lubricants, such as magnesium stearate and talc; binders, such as polyvinyl alcohol, hydroxypropyl cellulose, and gelatin; surfactants, such as a fatty acid ester; and plasticizers, such as glycerin.

(Oral Vaccine)

The transformed *Bifidobacterium* of the present invention having the WT1 protein expressed and displayed thereon can be suitably utilized as an oral vaccine. For example, the WT1 protein is recognized as an antigen on the wall of the intestinal tract, resulting in production of an antibody. Therefore, the transformed *Bifidobacterium* can serve as an effective oral vaccine. For example, each of acid-resistant-capsule formulations described below (a seamless capsule formulation, a soft capsule formulation, and a hard capsule formulation), when orally administered, passes through the stomach having a pH of from 1 to 3, without dissolving therein, to reach the intestines, and dissolves in the intestines. The transformed *Bifidobacterium* released from the formulation through the dissolution of the capsule maintains most protein structures even in the intestinal environment and expresses and displays the WT1 protein on the surface thereof.

When the transformed *Bifidobacterium* of the present invention is orally administered, the WT1 protein expressed on the surface of the *Bifidobacterium* is taken up by gut-associated lymphoid tissue (GALT), and is processed with an appropriate epitope by an antigen-presenting cell (APC) in the GALT. Further, it is considered that a peptide subjected to the processing in the GALT is displayed on the APC together with MHC class II or MHC class I, and induces a CTL having a T cell receptor specific to the peptide. It is considered that the APC activates CD8-positive T cells and CD4-positive T cells, and the actions of various cytokines, such as IL-2, released from the CD4-positive T cells, allow the growth of tumor cell-specific CD8-positive T cells (cytotoxic T cells (CTLs)). The WT1 protein of the present invention activates both the CD8-positive T cells and the CD4-positive T cells, and hence is considered to efficiently exhibit an anti-tumor effect on WT1-expressing tumor cells.

In addition, the oral vaccine including the transformed *Bifidobacterium* of the present invention as an active ingredient may include an adjuvant. The adjuvant has an action of boosting the effect of the vaccine. The adjuvant to be used for the oral vaccine of the present invention is preferably an adjuvant capable of boosting the induction of mucosal immunity, and examples thereof include, but not limited to: aluminum hydroxide and inorganic salts thereof; hydrocarbons, such as squalene and oil; bacterial toxins, such as cholera toxin, *E. coli* heat-labile enterotoxin B subunit (LTB), and lipid A from *Salmonella* (MPLA); polysaccharides, such as chitosan and inulin; and combinations thereof.

(Production of Acid-Resistant Capsule Formulation Containing Transformed *Bifidobacterium*)

The oral vaccine of the present invention preferably has the form of a capsule formulation. Herein, a capsule containing a content is referred to as "capsule formulation". The capsule formulation in the present invention includes a capsule coating and the transformed *Bifidobacterium* expressing the WT1 protein on the surface thereof, and the capsule coating is acid-resistant. The capsule formulation including the acid-resistant capsule coating and the transformed *Bifidobacterium* expressing the WT1 protein on the surface thereof may have any configuration and shape as long as the capsule formulation has the acid-resistant capsule coating and contains, as a capsule content, the transformed *Bifidobacterium* expressing the WT1 protein on the surface thereof. It is not excluded that the capsule formulation includes an additional constituent element. Therefore, the transformed *Bifidobacterium* expressing the WT1 protein on the surface thereof is included or encapsulated in the acid-resistant capsule coating (i.e., contained in the internal region of a capsule formed by the acid-resistant coating). The capsule formulation applicable to the transformed *Bifidobacterium* of the present invention may be produced by a method known per se or any method to be developed in the future.

In order for the transformed *Bifidobacterium* expressing the WT1 protein on the surface thereof to function as an oral vaccine, it is necessary that: the transformed *Bifidobacterium* pass through the stomach to reach the intestines; and the WT1 antigen protein and cell wall proteins of the *Bifidobacterium* be maintained even in the intestines. Incidentally, the pH of the stomach is from 1 to 3, and most proteins of the orally ingested *Bifidobacterium* are denatured owing to the markedly low pH. Therefore, in order that the transformed *Bifidobacterium* to be used in the present invention may reach the human intestines while maintaining various protein structures, and express and display the WT1 protein, it is preferred that the transformed *Bifidobacterium* be prevented from being affected by gastric acid to the extent possible.

Therefore, the oral vaccine including the transformed *Bifidobacterium* expressing the WT1 protein on the surface thereof to be used in the present invention is suitably a capsule formulation in which the transformed *Bifidobacterium* is included or encapsulated in an acid-resistant capsule coating, i.e., the transformed *Bifidobacterium* is contained inside a capsule formed of the acid-resistant coating. The configuration, shape, and the like of the capsule formulation are not particularly limited as long as the coating has resistance to gastric acid. That is, the capsule formulation is desirably configured such that gastric acid is prevented from entering the inside of the capsule to be brought into contact with the transformed *Bifidobacterium*. The capsule coating may be a coating that does not dissolve at a pH of 4 or less, preferably at a pH of from 1 to 3. A capsulation method is also not particularly limited.

II. Immunosuppression Inhibitor

The immunosuppression inhibitor in the present invention means a drug capable of inhibiting immunosuppression due to cancer cells. Some cancer cells control the function of T cells to cause a reduction in immune response in vivo. T cells that have been activated through the recognition of a cancer antigen enter a cancer tissue. Meanwhile, cancer cells express various immunosuppressive immune checkpoint molecules, or express ligands for immune checkpoint molecules. The immune checkpoint molecules and the like expressed by the cancer cells gradually cause immunosuppression of cancer-specific T cells. The immunosuppression inhibitor allows the cancer-specific T cells to be able to function normally.

An immune checkpoint inhibitor is suitably used as the immunosuppression inhibitor of the present invention. The immune checkpoint inhibitor is a drug that inhibits the activity of an immune checkpoint molecule expressed by a cancer cell. Examples of the immune checkpoint molecule include PD1, PD-L1, and CTLA4.

The active ingredient of the immune checkpoint inhibitor only needs to be one that recognizes any of the above-mentioned immune checkpoint molecules, and may be any of a low-molecular-weight compound, an antibody, a nucleic acid, a peptide, and the like. It is preferred that an antibody that specifically recognizes an immune checkpoint molecule be used as the active ingredient. The antibody that specifically recognizes an immune checkpoint molecule can bind to one kind or a plurality of kinds of the above-mentioned immune checkpoint molecules, thereby blocking or inhibiting the activity of the molecules. The immune checkpoint inhibitor in the present invention contains preferably at least one or more of an anti-PD1 antibody, an anti-PD-L1 antibody, and an anti-CTLA-4 antibody, more preferably an anti-PD1 antibody as the active ingredient. Specific examples of the immune checkpoint inhibitor containing the anti-PD1 antibody as the active ingredient include nivolumab, pembrolizumab, and pidilizumab. Specific examples of the anti-PD-L1 antibody include tremelimumab, AMP-224, MDX-1105, BMS-936559, MPLDL3280A, and MSB0010718C. A specific example of the anti-CTLA-4 antibody is ipilimumab.

The immunosuppression inhibitor may be administered in the form of any formulation. An administration route is not particularly limited, and oral administration or parenteral administration may be performed. Examples of the parenteral administration include subcutaneous injection, intramuscular injection, intracapsular injection, intraspinal injection, intraperitoneal injection, intratumoral injection, transdermal injection, and intravenous injection. As a formulation suitable for the parenteral administration, there are given, for example, an injection, an infusion, an inhalation, a spray, a suppository, a transdermal formulation, and a transmucosal formulation. As a formulation suitable for the oral administration, there are given, for example, a tablet, a granule, a fine granule, a powder, a syrup, a solution, a capsule, and a suspension.

The immunosuppression inhibitor may contain any pharmaceutically acceptable additive in addition to the active ingredient. Examples of the additive include, but not limited to, a carrier, an excipient, a stabilizing agent, a suspending agent, an emulsifier, a thickener, a dispersant, an absorption enhancer, a binder, a lubricant, a disintegrant, a wetting agent, a buffer, a taste-masking agent, a preservative, a colorant, a sugar, an oil, an antiseptic, a surfactant, a plasticizer, a diluent, an antioxidant, and a chelating agent that are pharmaceutically acceptable.

III. Modes of Combined Use of Transformed *Bifidobacterium* of the Present Invention with Immunosuppression Inhibitor The present invention also encompasses a method of preventing or treating a cancer, including using the transformed *Bifidobacterium* of the present invention in combination with an immunosuppression inhibitor. The cancer to be prevented or treated by the combined use of the transformed *Bifidobacterium* of the present invention with the immunosuppression inhibitor may be any cancer capable of highly expressing the WT1 protein, and may be solid cancer or hematopoietic cancer. The solid cancer is a malignant abnormal cell growth mass and may occur anywhere in the body, and examples thereof include prostate cancer, bladder cancer, lung cancer, stomach cancer, colorectal cancer, breast cancer, germ cell cancer, liver cancer, skin cancer, uterine cancer, cervical cancer, ovarian cancer, brain cancer, esophageal cancer, malignant mesothelioma, and renal cancer. Examples of the hematopoietic cancer include leukemia, myelodysplastic syndrome, multiple myeloma, and malignant lymphoma. The tumor to which the present invention is applicable is preferably solid cancer, more preferably any one selected from prostate cancer, bladder cancer, and lung cancer.

In the combined use of the transformed *Bifidobacterium* of the present invention with the immunosuppression inhibitor, the transformed *Bifidobacterium* and the immunosuppression inhibitor may be administered simultaneously or separately. The transformed *Bifidobacterium* and the immunosuppression inhibitor may each be administered in a single dose, or may be continuously administered. In the case of continuous administration, the respective numbers of times of administration of the transformed *Bifidobacterium* and the immunosuppression inhibitor may be the same or different from each other. Alternatively, the transformed *Bifidobacterium* may be administered separately from the immunosuppression inhibitor with an appropriate time interval before or after the immunosuppression inhibitor. In addition, the dosage forms and administration routes of the transformed *Bifidobacterium* and the immunosuppression inhibitor do not need to be the same, and may be different from each other. For example, the following is also permitted: the transformed *Bifidobacterium* is orally administered, and the immunosuppression inhibitor is parenterally administered. The transformed *Bifidobacterium* and the immunosuppression inhibitor to be used in combination may each be used as a single agent, or may be used as a kit formulation by being combined with each other.

The doses of the transformed *Bifidobacterium* and the active ingredient of the immunosuppression inhibitor vary depending on, for example, the body weight and age of the subject, symptoms, and an administration method, but could be appropriately selected by a person skilled in the art. In addition, the doses may be separately selected for the transformed *Bifidobacterium* and the immunosuppression inhibitor. The number of times of the administration of each of the transformed *Bifidobacterium* and the immunosuppression inhibitor is not particularly limited, but the administration is preferably performed a plurality of times. It is considered that, in the combination therapy of the present invention, the administration of the transformed *Bifidobacterium* induces tumor-specific T cells, and the immunosuppression inhibitor cancels the immunosuppression of tumor-specific T cells. Therefore, the transformed *Bifidobacterium* is preferably administered prior to the administration of the immunosuppression inhibitor. The phrase "administered prior" means that an effective dose of the transformed *Bifidobacterium* is administered at least 1 or more times before the immunosuppression inhibitor. Specifically, the combined use of the immunosuppression inhibitor may be initiated after from 1 day to 3 weeks, preferably from about 1 week to about 2 weeks from the initiation of the oral administration of the transformed *Bifidobacterium*. The administration of the two agents may be performed until the cancer becomes resistant to the treatment or the cancer disappears.

EXAMPLES

The present invention is specifically described below by way of Reference Example and Examples. However, the present invention is not limited to Reference Example and Examples below.

Example 1: Generation of *Bifidobacterium* Displaying GL-BP-WT1 on Surface Thereof A. Isolation of GL-BP Gene A GL-BP gene was amplified from *Bifidobacterium longum* JCM1217 (ATCC15707) genome (Accession: EU193949) by performing a PCR reaction using primers glt-f: 5'-ggggtgctgatatattggtttg-3' (SEQ ID NO: 3) and glt-r: 5'-gctcgagctcggaaacagacaggccgaagtt-3' (SEQ ID NO: 4) which allowed the stop codon to be substituted with XhoI, and KOD-Plus- (manufactured by Toyobo Co., Ltd.). PCR products including the amplified GL-BP gene were subjected to agarose gel electrophoresis to excise a 1, 989 bp PCR product, and only a GL-BP gene amplification fragment was isolated and purified using Wizard SV Gel and PCR Clean-Up System (manufactured by Promega).

B. Construction of pMW118 Plasmid Having Isolated GL-BP Gene

The isolated and purified GL-BP gene amplification fragment was introduced into the SmaI site of pMW118 having an ampicillin resistance gene (Ampr) (manufactured by Nippon Gene Co., Ltd.) to construct a plasmid. DNA Ligation Kit Ver. 2 (manufactured by Takara Bio Inc.) was used for ligation. The constructed plasmid was transferred into *E. coli* DH5a (manufactured by Takara Bio Inc.) by a heat shock method (42° C., 30 seconds). The resultant was applied to an LB agar medium containing 100 µg/ml of ampicillin (manufactured by Difco), and was cultured at 37° C. overnight to provide transformed *E. coli* harboring a plasmid having a GL-BP gene. The plasmid was extracted and purified from the transformed *E. coli* using Quantum Prep Plasmid Miniprep Kit (manufactured by Bio-Rad), and its sequence was confirmed by sequencing. Thus, the recombinant plasmid having introduced therein the GL-BP gene was obtained. The obtained recombinant plasmid was named pJT101.

C. Isolation of WT1 Gene

DNA encoding an amino acid sequence from position 117 to position 439 of murine WT1 (SEQ ID NO: 2) was obtained by total synthesis (Funakoshi Co., Ltd.). In the synthesis, codons frequently used in a *Bifidobacterium* were used. In addition, an XhoI recognition sequence (CTCGAG: SEQ ID NO: 5) was added to the N-terminus side, and a stop codon and a succeeding SphI recognition sequence (GCATGC: SEQ ID NO: 6) were added to the C-terminus side. The DNA was introduced into the SmaI site of a pUC18 vector to construct a plasmid. DNA Ligation Kit Ver. 2 (manufactured by Takara Bio Inc.) was used for ligation. The constructed plasmid was transferred into *E. coli* DH5a (manufactured by Takara Bio Inc.) by a heat shock method (42° C., 30 seconds). The resultant was applied to an LB agar medium containing 100 µg/ml of ampicillin (manufactured by Difco), and was cultured at 37° C. overnight to provide transformed E. coli harboring a plasmid having DNA encoding murine WT1 (117 to 439). The plasmid was extracted and purified from the transformed E. coli using Quantum Prep Plasmid Miniprep Kit (manufactured by Bio-Rad), and its sequence was confirmed by sequencing. The obtained recombinant plasmid was named pTK2875-1.

```
Sequence of synthesized murine WT1 gene
                                         (SEQ ID NO: 2)
CTCGAGCCGTCCCAGGCGTCGTCGGGCCAGGCGAGGATGTTCCCGAAC

GCGCCCTACCTGCCCAGCTGCCTGGAGTCCCAGCCGACGATCCGCAAC

CAGGGCTACTCCACCGTGACGTTCGACGGCGCCCCGTCCTACGGCCAC

ACGCCCAGCCACCACGCCGCCCAGTTCCCGAACCACAGCTTCAAGCAC

GAAGACCCCATGGGCCAGCAGGGCAGCCTCGGCGAACAGCAGTACAGC

GTGCCGCCGCCGGTCTACGGCTGCCACACCCCGACCGACTCCTGCACG

GGCTCCCAGGCCCTGCTCCTGCGTACGCCGTACTCCTCCGACAACCTC

TACCAGATGACCTCCCAGCTGGAGTGCATGACCTGGAACCAGATGAAC

CTGGGCGCCACGCTGAAGGGAATGGCCGCGGGGTCGTCGAGCTCCGTC

AAGTGGACCGAAGGCCAGTCCAACCACGGCATCGGCTACGAGTCCGAG

AACCACACCGCGCCGATCCTGTGCGGAGCCCAGTACCGCATCCACACG

CACGGCGTCTTCCGCGGCATCCAGGACGTCCGGCGCGTCTCCGGCGTC

GCGCCGACCCTGGTGCGGTCCGCCTCCGAGACCTCCGAGAAGCGCCCG

TTCATGTGCGCCTACCCGGGCTGCAACAAGCGCTACTTCAAGCTCTCG

CACCTGCAGATGCACTCCCGGAAGCACACCGGCGAGAAGCCGTACCAG

TGCGACTTCAAGGACTGCGAACGCCGCTTCTCGCGCAGCGACCAGCTG

AAGCGCCACCAGCGTAGGCACACCGGCGTGAAGCCCTTCCAGTGCAAG

ACCTGCCAGCGCAAGTTCTCCCGCAGCGACCACCTCAAGACGCACACC

CGCACCCACACCGGCAAGACGTCCGAGAAGCCGTTCTCGTGCCGCTGG

CACAGCTGCCAGAAGAAGTTCGCCCGCAGCGACGAGCTCGTGCGCCAC

CACAACATGCACCAGTGAAGCATGC
```

A plasmid having DNA encoding an amino acid sequence from position 117 to position 350 of murine WT1 was generated as described below. That is, with the use of the pTK2875 obtained above as a template, a PCR reaction was performed using a primer WT1-f (5'-CGCTCGAGCCGTCCCAGGCGTCGT-3': SEQ ID NO: 7) and a primer WT1-r2 (5'-GCGCATGCT-CACTCGCCGGTGTGCTTCCGG-3': SEQ ID NO: 8), and KOD-Plus- (manufactured by Toyobo Co., Ltd.), to amplify a DNA fragment encoding murine WT1 (117 to 350). A stop codon and a succeeding SphI recognition sequence (GCATGC: SEQ ID NO: 6) were added to the C-terminus side. The amplified PCR products were subjected to agarose gel electrophoresis to excise a 721 bp PCR product, which was isolated and purified using Wizard SV Gel and PCR Clean-Up System (manufactured by Promega). The isolated and purified product was introduced into the SmaI site of a pUC18 vector to construct a plasmid. DNA Ligation Kit Ver. 2 (manufactured by Takara Bio Inc.) was used for ligation. The constructed plasmid was transferred into E. coli DH5a (manufactured by Takara Bio Inc.) by a heat shock method (42° C., 30 seconds). The resultant was applied to an LB agar medium containing 100 µg/ml of ampicillin (manufactured by Difco), and was cultured at 37° C. overnight to provide transformed E. coli harboring a plasmid having DNA encoding murine WT1 (117 to 350). The plasmid was extracted and purified from the transformed E. coli using Quantum Prep Plasmid Miniprep Kit (manufactured by Bio-Rad), and its sequence was confirmed by sequencing. The obtained recombinant plasmid was named pTK2875-2.

D. Construction of Plasmid Having WT1 Gene Downstream of GL-BP Gene

The plasmids pTK2875-1 and pTK2875-2 each harboring the WT1 gene obtained in the section C. were treated with restriction enzymes XhoI and SphI and subjected to agarose gel electrophoresis to excise 986 bp and 718 bp DNA fragments, respectively, which were isolated and purified using Wizard SV Gel and PCR Clean-Up System (manufactured by Promega). Those WT1 gene amplification fragments were introduced into the above-mentioned pJT101 plasmids, which had also been treated with restriction enzymes XhoI and SphI, respectively, using DNA Ligation Kit Ver. 2, to construct plasmids. Each of the constructed plasmids was transferred into E. coli DH5a by a heat shock method. The resultant was applied to an LB agar medium containing 100 µg/ml of ampicillin, and was cultured at 37° C. overnight to provide transformed E. coli harboring a plasmid having a fusion gene of the GL-BP gene and the WT1 gene (FIG. 1). The plasmid was extracted and purified from the obtained transformed E. coli using Quantum Prep Plasmid Miniprep Kit, and its sequence was confirmed by sequencing. Thus, a recombinant plasmid having the WT1 gene linked downstream of the GL-BP gene was obtained. The obtained recombinant plasmids were named pTK2895 (GLBP-WT1 (117 to 439)) and pTK2896 (GLBP-WT1 (117 to 350)), respectively.

E. Construction of E. coli-Bifidobacterium Shuttle Vector

As an E. coli-Bifidobacterium shuttle vector, the E. coli-Bifidobacterium shuttle vector pJW241 disclosed in Vaccine. 28:6684-6691 (2010) was used.

F. Integration of Gene Having GL-BP Gene and WT1 Gene Linked to Each Other into E. coli-Bifidobacterium Shuttle Vector pJW241

With the use of each of the vectors pTK2895 (GLBP-WT1 (117 to 439)) and pTK2896 (GLBP-WT1 (117 to 350)) each having the fusion gene having the GL-BP gene and the WT1 gene linked to each other (hereinafter referred to as "this fusion gene") as a template, PCR was performed using a primer Infusion-F (5'-ggaaaactgtccatagatggcgaggcgaacgc-cacg-3': SEQ ID NO: 9) and a primer Infusion-R (5'-tttcatctgtgcatagtgctgcaaggcgattaagtt-3': SEQ ID NO: 10). The PCR amplified products were subjected to agarose gel electrophoresis to excise this fusion gene, which was isolated and purified using Wizard SV Gel and PCR Clean-Up System (manufactured by Promega). In addition, separately from the foregoing, the E. coli-Bifidobacterium shuttle vector pJW241 (Vaccine. 28:6684-6691 (2010)) was treated with restriction enzyme NdeI. This fusion gene that had been purified and the pJW241 were each ligated using In-Fusion HD Cloning Kit (manufactured by Clontech), and the obtained plasmid was transferred into E. coli DH5a by a heat shock method. The resultant was applied to an LB agar medium containing 70 µg/ml of spectinomycin, and was cultured at 37° C. overnight to provide transformed E. coli harboring a plasmid having the origin of replication, i.e., ori region of E. coli, a spectinomycin resistance gene (SPr), the origin of replication, i.e., ori region of Bifidobacterium, and this fusion gene. The plasmid was extracted and purified from the transformed *E. coli* using Quantum Prep Plasmid Miniprep Kit, and the presence of the sequence of this fusion gene was confirmed. The obtained recombinant plasmids were named pTK2897 (GLBP-WT1 (aa 117 to 439)) and pTK2898 (GLBP-WT1 (aa 117 to 350)), respectively.

G. Preparation of Host *Bifidobacterium* Liquid

*Bifidobacterium longum* 105-A (Matsumura H. et al., Biosci. Biotech. Biochem., 1997, vol. 61, pp. 1211-1212: donated by Tomotari Mitsuoka, a professor emeritus at the University of Tokyo) was inoculated on 50 ml of a GAM medium (manufactured by Nissui Pharmaceutical Co., Ltd.), and was cultured at 37° C. using AnaeroPack™ Kenki (manufactured by Mitsubishi Gas Chemical Company, Inc.). During the culture, an absorbance at a wavelength of 600 nm was measured, and the culture was terminated when the absorbance reached from 0.4 to 0.8. After the completion of the culture, centrifugation (6,000×g, for 10 minutes) was performed with a high-speed centrifuge to collect the bacterial cells. The collected bacterial cells were washed two or three times by adding 10 ml of a 10% (v/v) glycerol solution to suspend the bacterial cells and centrifuging the suspension with a high-speed centrifuge.

H. Generation of *Bifidobacterium* Displaying GL-BP-WT1 Fusion Protein on Surface Thereof by Transformation of *Bifidobacterium* with Recombinant Plasmids pTK2897 and pTK2898

The host *Bifidobacterium* liquid obtained in the section G. was suspended by adding 500 μl of a 10% (v/v) glycerol solution thereto. 200 μl of the suspension was taken in a separate tube, and 5 μl of each of solutions respectively containing the recombinant plasmids pTK2897 and pTK2898 obtained in the section F. was added. The contents were mixed, and the whole was left to stand on ice for 5 minutes. Then, the mixed liquid was placed in a 0.2 cm electroporation cuvette (manufactured by Bio-Rad) and subjected to electroporation using a Gene Pulser Xcell electroporation system (manufactured by Bio-Rad) under the conditions of 2 kV, 2.5 μF, and 200Ω. Immediately after the electroporation, 0.8 ml of a GAM medium that had been adjusted to 37° C. in advance was added, and the cells were cultured at 37° C. for 3 hours using AnaeroPack™ Kenki. Then, the resultant was applied to a GAM agar medium containing 70 μg/ml of spectinomycin (manufactured by Nissui Pharmaceutical Co., Ltd.), and was cultured at 37° C. using AnaeroPack™ Kenki to provide transformed *Bifidobacterium*. The obtained transformed *Bifidobacterium* was inoculated on a GAM medium containing 70 μg/ml of spectinomycin, and was cultured at 37° C. using AnaeroPack™ Kenki. After the completion of the culture, the culture broth was dispensed into a 1.5 ml tube and suspended by adding an equal amount of a 50% (v/v) glycerol solution. The resultant suspension was stored at −80° C. to generate a frozen stock, and the frozen stock was used as master cells of *Bifidobacterium* displaying a GL-BP-WT1 fusion protein on the surface thereof (sometimes referred to as "transformed *Bifidobacterium*") (TK2900 (GLBPWT1 (aa 117 to 439)) and TK2903 (GLBP-WT1 (aa 117 to 350)), respectively).

Figure 2:
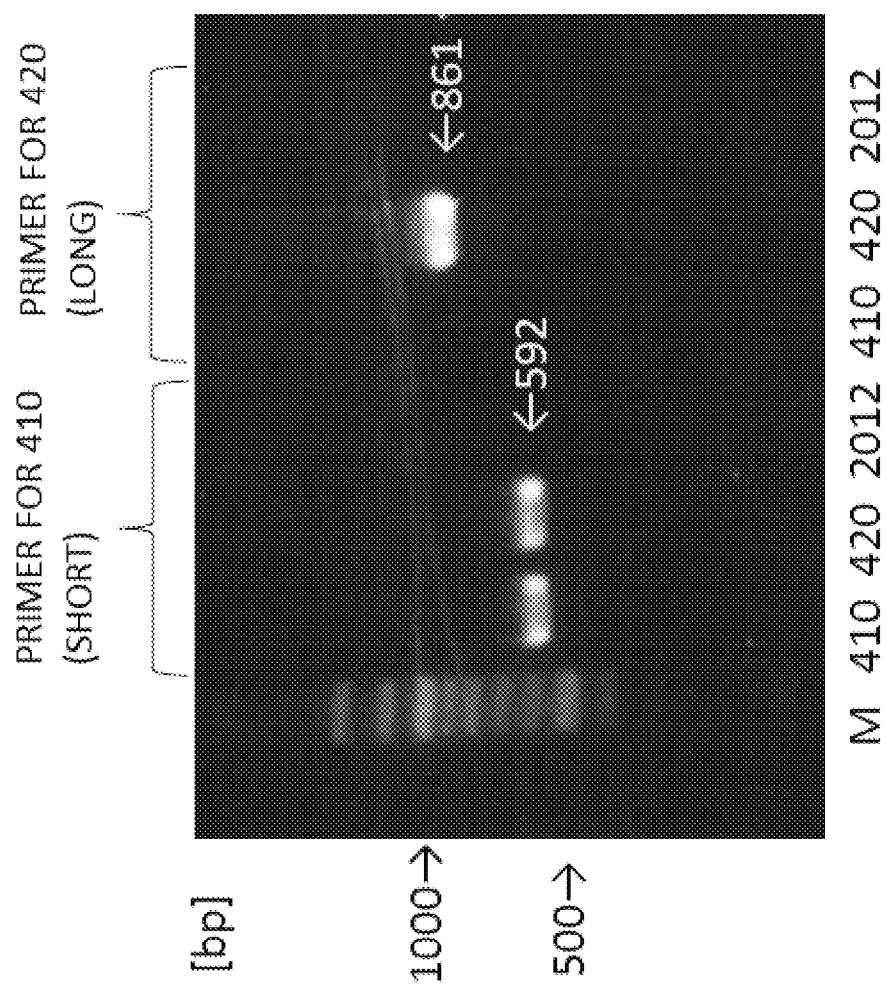
FIG. 2 is a photographic image for showing results of confirmation of DNA encoding WT1 transferred into a transformed *Bifidobacterium* (Example 1).

FIG. 2 is an image for showing results of confirmation by electrophoresis of the lengths of amplified fragments obtained by amplifying the gene (DNA) of each recombinant *Bifidobacterium* by PCR using the following primers.

```
Forward primer 410, 420:
                                    (SEQ ID NO: 11)
ACGATCCGCAACCAGGGCTACTC Reverse primer 410:
                                    (SEQ ID NO: 12)
ggtgcgagagcttgaagtagcgc Reverse primer 420:
                                    (SEQ ID NO: 13)
gtcgctgcgggcgaacttcttc
```

410 represents *B. longum* 410, which is a *Bifidobacterium* transformed with a shuttle vector having inserted therein DNA encoding murine WT1 (aa 170 to 350) and corresponds to the TK2903 (GLBP-WT1 (aa 117 to 350)). 420 represents *B. longum* 420, which is a *Bifidobacterium* transformed with a shuttle vector having inserted therein DNA encoding murine WT1 (aa 117 to 439) and corresponds to the TK2900 (GLBP-WT1 (aa 117 to 439)). 2012 represents *B. longum* 2012, which is a *Bifidobacterium* transformed with a shuttle vector having inserted therein only a GLBP gene without having inserted therein DNA encoding murine WT1. The primers denoted by 410 amplify the DNA encoding murine WT1 (aa 117 to 350), and the primers denoted by 420 amplify the DNA encoding murine WT1 (aa 117 to 439).

It was confirmed from the results of FIG. 2 that the DNA encoding WT1 was certainly transferred into each recombinant *Bifidobacterium*.

Example 2: Confirmation of Displaying of GL-BP-WT1 Fusion Protein of Transformed *Bifidobacterium* on Surface Thereof (1) Each transformed *Bifidobacterium* obtained in Example 1 described above was centrifuged with a high-speed centrifuge to collect the bacterial cells. The collected bacterial cells were washed three times by adding PBS thereto to suspend the bacterial cells and centrifuging the suspension with a high-speed centrifuge. To the bacterial cells, a solution containing PBS, 1 M Tris-HCl (pH 8.0) (manufactured by Nippon Gene Co., Ltd.), and Triton X-100 (manufactured by Wako Pure Chemical Industries, Ltd.) was added, and the whole was left to stand on ice for 30 minutes. To the resultant solution, an equal amount of a 2×SDS gel electrophoresis buffer was added, and the whole was left to stand at 95° C. for 5 minutes to provide a sample for electrophoresis. Then, 8% (w/v) acrylamide gel was set in an electrophoresis apparatus (manufactured by ATTO Corporation), and the obtained sample was applied and subjected to electrophoresis along with a molecular weight marker at a current of 20 mA for 1.5 hours. The gel after the electrophoresis was placed on a nitrocellulose membrane (manufactured by ATTO Corporation) and subjected to blotting with a blotting apparatus (manufactured by Bio-Rad) by applying a current of 20 mA thereto. After the blotting, the nitrocellulose membrane was subjected to blocking by being immersed in TBS (manufactured by Nippon Gene Co., Ltd.) serving as a buffer containing 4% (w/v) skim milk (manufactured by BD) for 1 hour. After the blocking, the nitrocellulose membrane was washed twice with TBS. After the washing, the nitrocellulose membrane was immersed in TBS supplemented with a 0.5% (w/v) primary antibody (WT1 antibody (C-19): sc-192: manufactured by Santa Cruz Biotechnology) for 1.5 hours, and was washed three times with TBS. Then, the nitrocellulose membrane was immersed in TBS supplemented with a 0.5% (w/v) secondary antibody (goat anti-rabbit IgG-HRP: sc-2004: manufactured by Santa Cruz Biotechnology) for 3 hours. Then, the nitrocellulose membrane was washed three times with TBS, allowed to develop a color using a 1-Steptm NBT/BCIP plus Suppressor kit (manufactured by Pierce) for 30 minutes under a light-shielding condition, and rinsed with pure water. After that, the surface expression of the GL-BP-WT1 fusion protein was confirmed on the basis of the developed color.

Figure 3A:
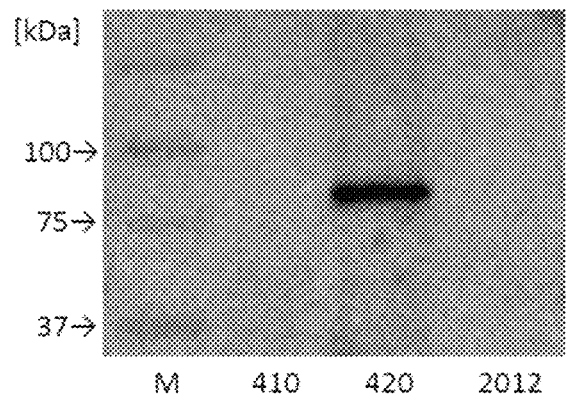
FIGS. 3A and 3B are photographic images for showing: results of confirmation by western blotting of a WT1 protein expressed on the surface of the transformed *Bifidobacterium* of the present invention (FIG. 3A); and results of confirmation thereof by immunofluorescence staining (FIG. 3B) (Example 2).

The results of the western blotting are shown in FIG. 3A. As apparent from FIG. 3A, *B. longum* 420 showed a clear band at 82.9 kDa corresponding to the sum of the molecular weights of WT1 (aa 117 to 439) and the GL-BP fusion protein. Therefore, it was confirmed that the transformed *Bifidobacterium* (*B. longum* 420) expressed the GL-BP-WT1 fusion protein.

(2) Each transformed *Bifidobacterium* obtained in Example 1 described above that had been cultured was centrifuged with a high-speed centrifuge to collect the bacterial cells. The collected bacterial cells were washed three times by adding PBS (manufactured by Nippon Gene Co., Ltd.) serving as a buffer thereto to suspend the bacterial cells and centrifuging the suspension with a high-speed centrifuge. Then, PBS containing 1% (w/v) BSA supplemented with a primary antibody (WT1 antibody (C-19): sc-192: manufactured by Santa Cruz Biotechnology) was added to the *Bifidobacterium* liquid to suspend the cells, and the suspension was left to stand at 37° C. for 30 minutes. The bacterial liquid that had been left to stand for 30 minutes was centrifuged with a high-speed centrifuge to collect the bacterial cells. The collected bacterial cells were washed twice by adding PBS thereto to suspend the bacterial cells and centrifuging the suspension with a high-speed centrifuge. Then, PBS containing 1% (w/v) BSA supplemented with a secondary antibody Alexa Fluor™ 488 Rabbit Anti-Mouse IgG antibody (manufactured by Molecular Probes) was added to the *Bifidobacterium* liquid to suspend the cells, and the suspension was left to stand at 37° C. for 30 minutes. The bacterial liquid that had been left to stand for 30 minutes was centrifuged with a high-speed centrifuge to collect the bacterial cells. The collected bacterial cells were washed twice by adding PBS thereto to suspend the bacterial cells and centrifuging the suspension with a high-speed centrifuge, and were then observed with a fluorescence microscope (manufactured by Keyence Corporation).

Figure 3B:
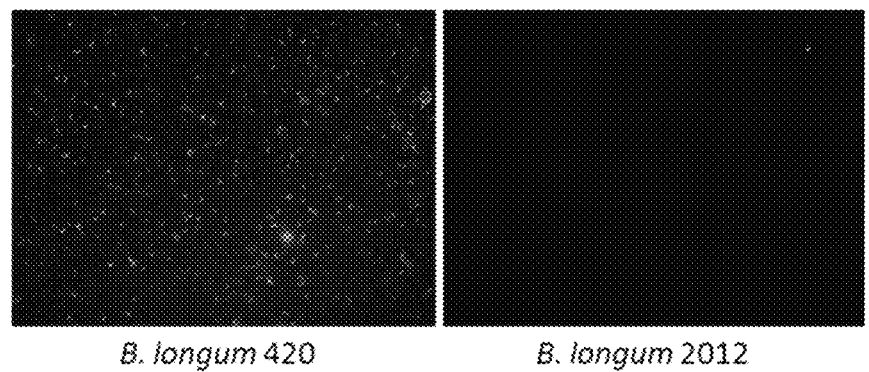

The results of the observation with the fluorescence microscope are shown in FIG. 3B. The left-hand side of FIG. 3B is a fluorescence micrograph of *B. longum* 420, which is a transformed *Bifidobacterium* obtained in Example 1 described above, and the right-hand side of FIG. 3B is a fluorescence micrograph of *B. longum* 2012. It was confirmed from the fluorescence micrographs that WT1 was present on the cell surface of *B. longum* 420.

Example 3: Confirmation of Cellular Immune Response-Inducing Effect of Oral Administration of GL-BP-WT1 Fusion Protein of Transformed *Bifidobacterium*

Figure 4:
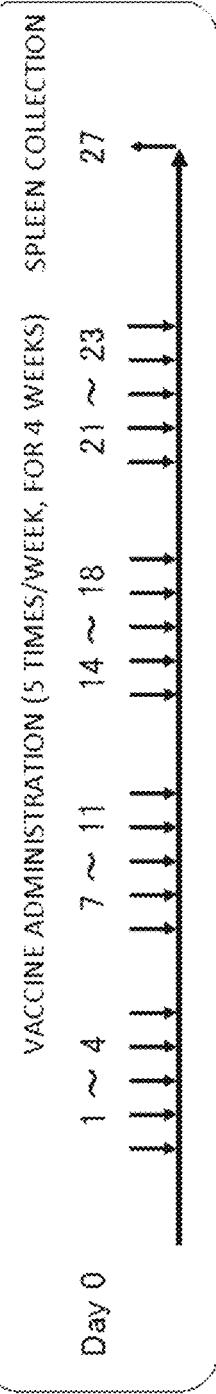
FIG. 4 is a diagram for illustrating an experimental protocol for confirming the cellular immune response-inducing effect of the transformed *Bifidobacterium* of the present invention through the use of mice (Example 3).
Figure 5:
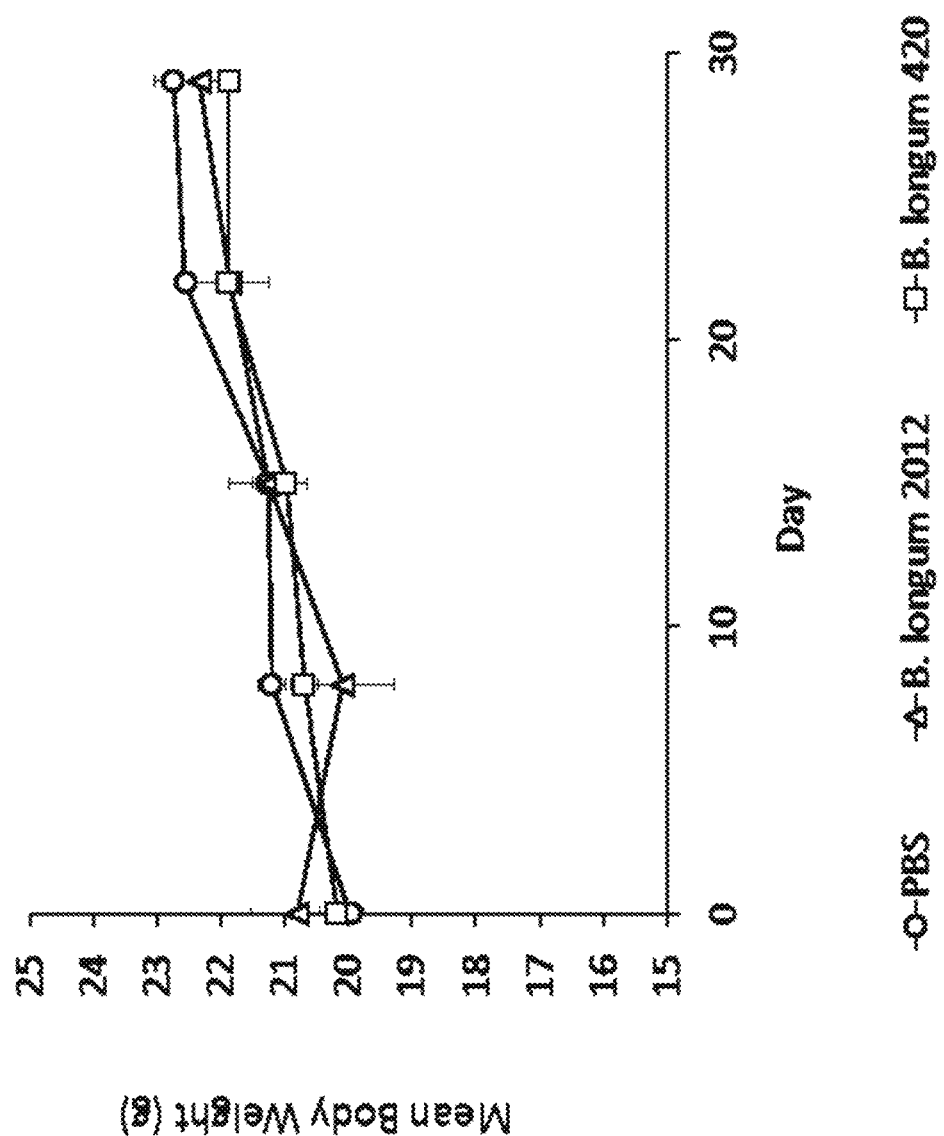
FIG. 5 is a graph for showing results of confirmation of the influence of the administration of the transformed *Bifidobacterium* of the present invention on the body weight of mice (Example 3).

A cellular immune response-inducing effect achieved when the frozen stock of each transformed *Bifidobacterium* obtained in Example 1 described above was orally administered to mice was confirmed. An experimental protocol is illustrated in FIG. 4. During the observation period from Day 0 to Day 29, the mean body weight of the *B. longum* 420-administered group changed similarly to those in the other groups (FIG. 5), and side effects, such as diarrhea and a behavioral defect, of the administration of *B. longum* 420 were not observed.

(1) On Day 27, the spleen was collected from each of the mice to prepare splenocytes. The splenocytes were cultured, and the concentrations of various cytokines of the cellular immune system in the splenocyte culture supernatant were measured. A C1498 murine leukemia cell line having a murine WT1 gene transferred thereinto so as to express a murine WT1 protein (C1498-WT1 cells) was used as an antigen for stimulating the splenocytes, and C1498 cells having transferred thereinto an empty vector not having inserted therein the murine WT1 gene (C1498-Mock cells) were used as a control.

$4 \times 10^5$ cells/well of the murine splenocytes were subjected to stimulated culture with mitomycin C-treated C1498-WT1 cells or C1498-Mock cells ($4 \times 10^4$ cells/well in each case) in a 96-well plate at 37° C. for 3 days (n=5). After the culture, the cell culture broth was recovered, and the concentrations of various cytokines (interferon-$\gamma$ (IFN-$\gamma$), interleukin-2 (IL-2), and tumor necrosis factor $\alpha$ (TNF-$\alpha$)) were measured by an enzyme-linked immuno sorbent assay (ELISA) method. The measurement of the concentrations of the various cytokines was performed using Mouse IFN-gamma Quantikine ELISA Kit (R&D Systems, Minneapolis, Minn.), Mouse TNF-alpha Quantikine (R&D Systems), and Mouse IL-2 ELISA Kit (Thermo Scientific, Waltham, Mass.) by methods in conformity to the manuals of the kits.

Figure 6:
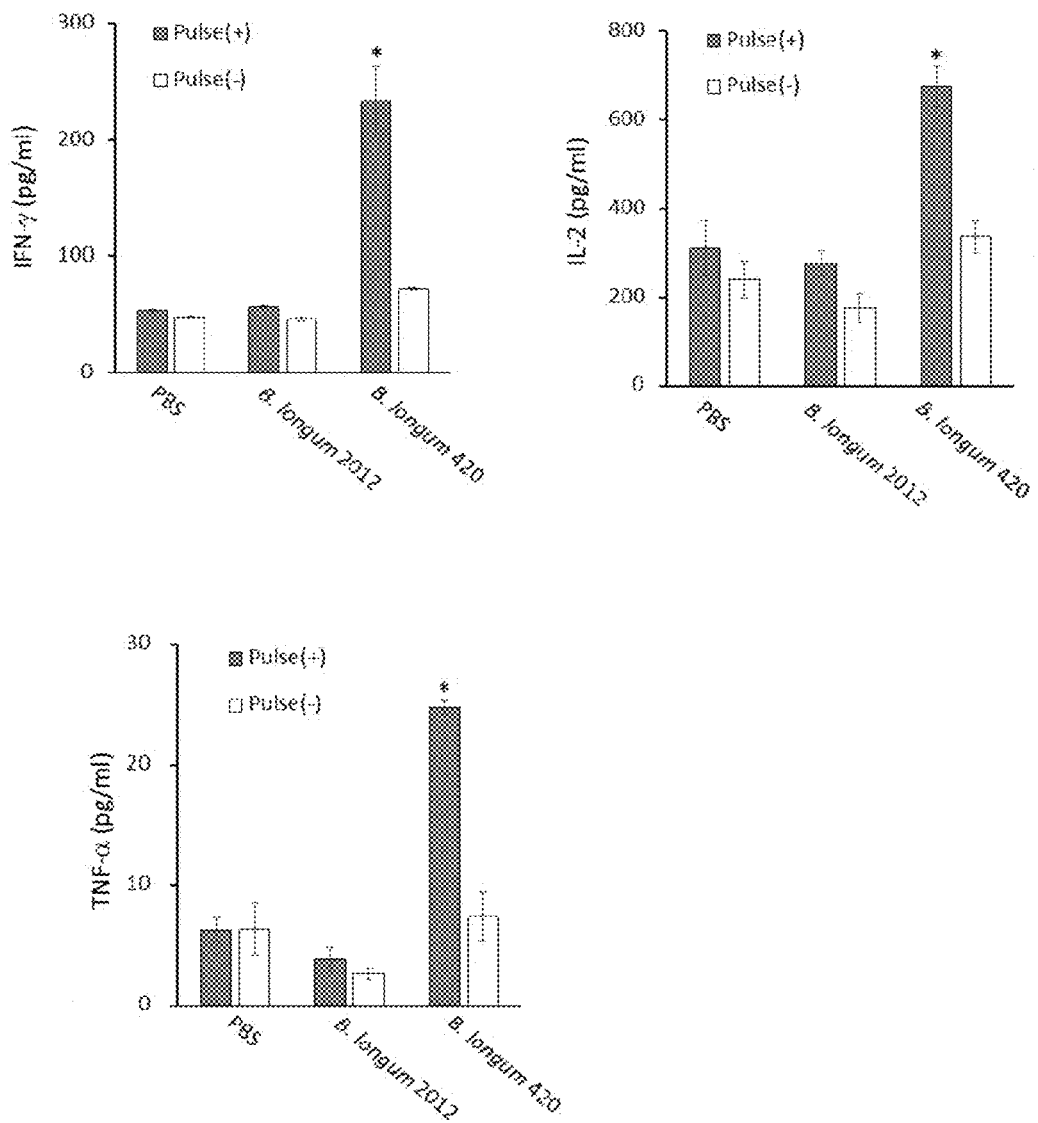
FIG. 6 are graphs for showing results of confirmation of the influence of the transformed *Bifidobacterium* of the present invention on cytokine production capacity (Example 3).

The results are shown in FIG. 6. In the *B. longum* 420-administered group, the production amounts of IFN-$\gamma$, IL-2, and TNF-$\alpha$ were significantly increased by restimulation with the C1498-WT1 cells as compared to those in the non-stimulated group (*: $p<0.01$). The production amount of IFN-$\gamma$ in the *B. longum* 420-administered group was significantly increased as compared to those in the PBS-administered group and the *B. longum* 2012-administered group (*: $p<0.01$). Therefore, it was shown that, as a result of the oral administration of the GL-BP-WT1 fusion protein of the transformed *Bifidobacterium*, the production of various cytokines important for WT1-specific anti-tumor immunity was boosted by stimulation with the WT1 protein.

(2) Splenocytes prepared in the same manner as in the section (1) were subjected to intracellular cytokine staining (ICCS) to confirm the ratio of cytokine-producing T cells in CD4-positive T cells or CD8-positive T cells.

The murine splenocytes ($2 \times 10^6$ cells/well, n=5) were mixed with $2 \times 10^5$ cells/well of the C1498-WT1 cells, and the cells were cultured in a 24-well plate under the conditions of 37° C. and 5% $CO_2$ for 42 hours. At this time, GolgiStop or GolgiPlug (BD) was added to each well, and the cells were further cultured for 6 hours. The cells were recovered, and subjected to intracellular cytokine staining using BD/Cytofix/Cytoperm Plus Fixation/Permeabilization Kit (BD). An FITC-labeled anti-CD3 monoclonal antibody, an FITC-labeled anti-CD8 monoclonal antibody, or an FITC-labeled anti-CD4 monoclonal antibody was added, followed by mixing. The cells were washed with a buffer for staining. Various anti-cytokine antibodies were added to the cells, and the cells were gently suspended. After that, the whole was left to stand still in a dark place at room temperature. The cells were washed, and then resuspended in a buffer for staining. After that, the cells were analyzed with a flow cytometer using analysis software included therewith. A specific method performed was in conformity to the manual of the kit.

Figure 7:
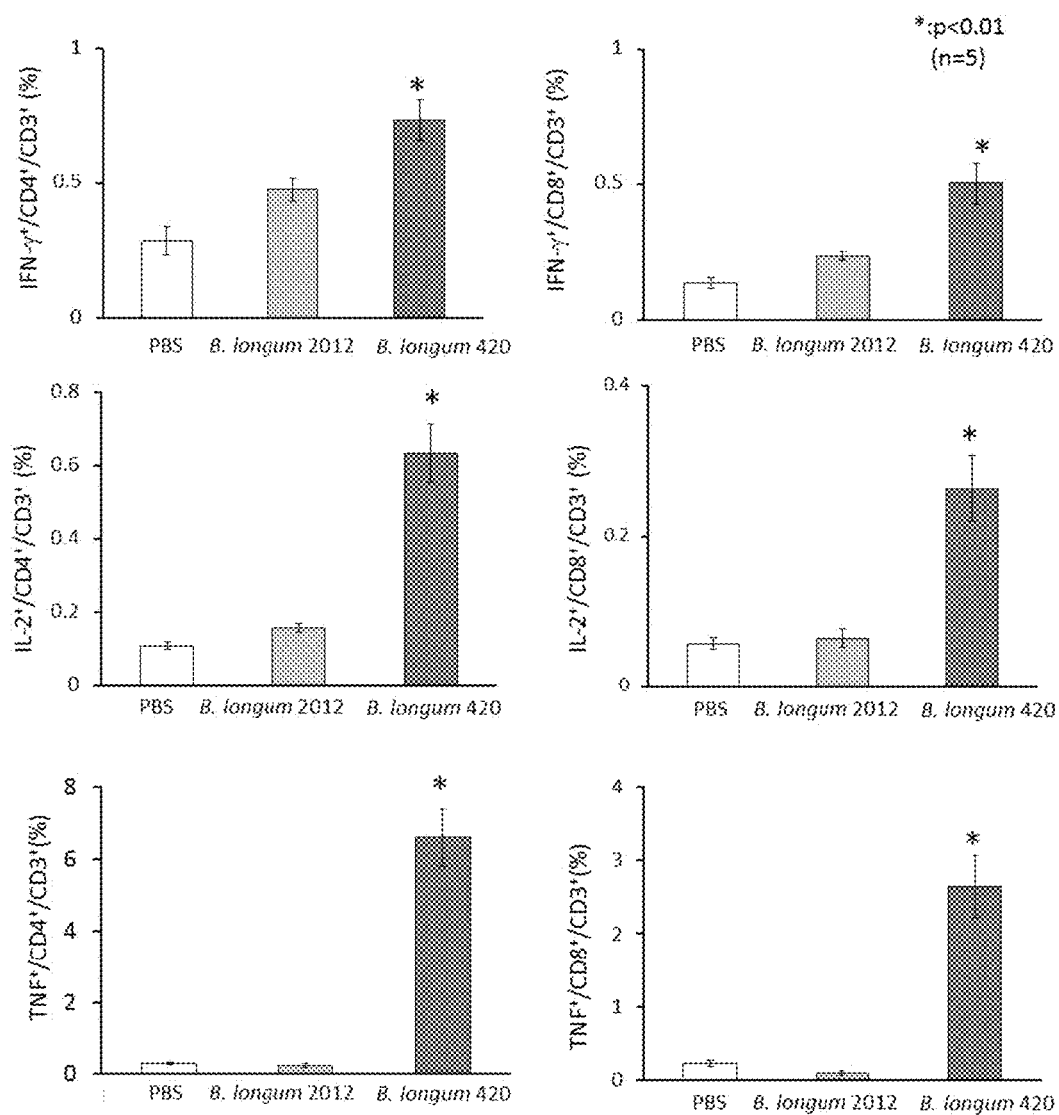
FIG. 7 are graphs for showing results of confirmation of the influence of the transformed *Bifidobacterium* of the present invention on activated T cell induction capacity (Example 3).

The results are shown in FIG. 7. In the *B. longum* 420-administered group, both the CD4+T cells and CD8+T cells that produced IFN-γ, IL-2, and TNF in the splenocytes significantly increased as compared to those in the other administered groups (*: p<0.05). Therefore, it was shown that the oral administration of the GL-BP-WT1 fusion protein of the transformed *Bifidobacterium* increased the CD4$^+$T cells and CD8$^+$T cells that produced cytokines involved in WT1-specific cellular immunity.

(3) For splenocytes prepared in the same manner as in the section (1), the ratio of WT1 (db126 peptide)-specific CD8$^+$T cells in CD8-positive T cells was confirmed using a WT1 tetramer.

$2 \times 10^6$ cells/well of the murine splenocytes (n=5) were mixed with $2 \times 10^5$ cells/well of the C1498-WT1 cells, and the cells were cultured in a 24-well plate under the conditions of 37° C. and 5% $CO_2$ for 7 days. On the 1st day and the 3rd day of the culture, 20 IU/ml of IL-2 was added to induce CTLs. After the culture, CD8-positive T cells were detected using an FITC-labeled anti-CD3 monoclonal antibody and an FITC-labeled anti-CD8 monoclonal antibody, and WT1 peptide-specific CD8$^+$T cells (CTLs) were detected using H-2db WT1 Tetramer-RMFPNAPYL (MBL). The cells were analyzed with a flow cytometer using analysis software included therewith.

Figure 8:
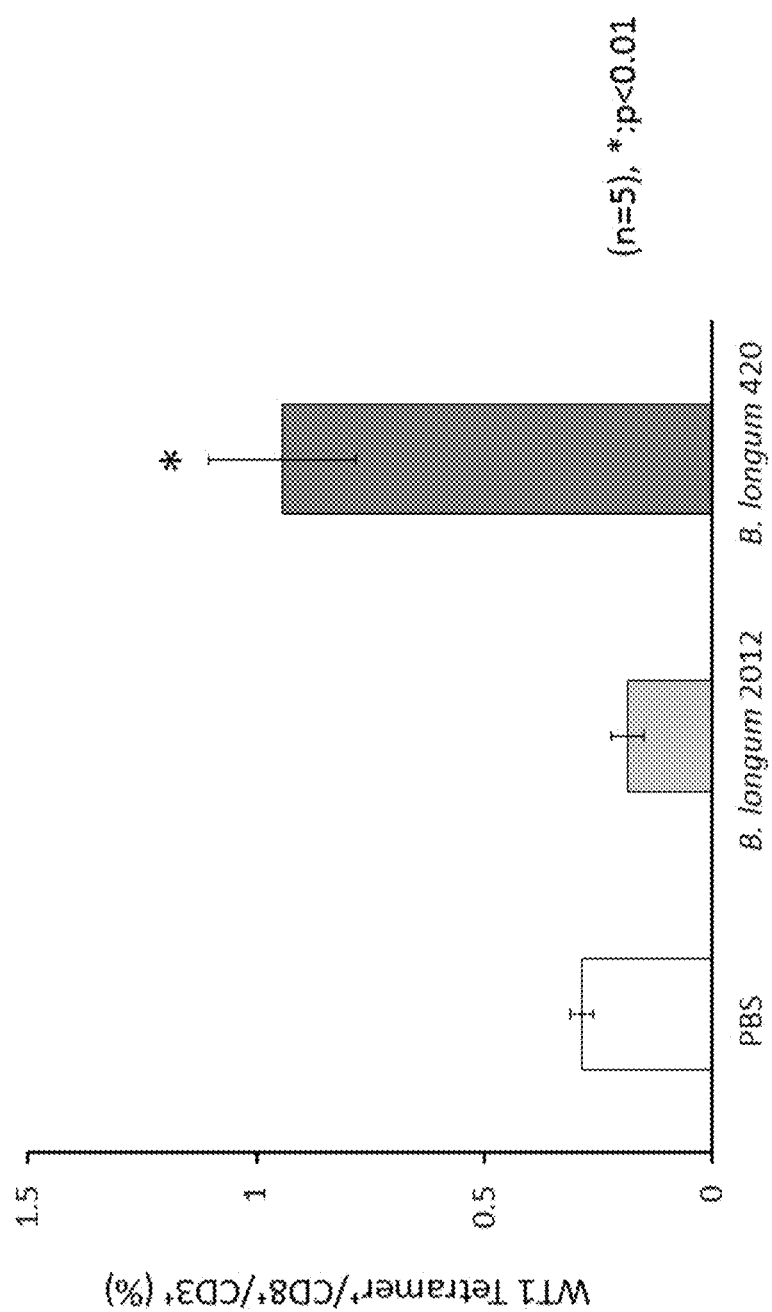
FIG. 8 is a graph for showing results of confirmation of the WT1-specific CTL induction capacity of the transformed *Bifidobacterium* of the present invention (Example 3).

The results are shown in FIG. 8. When the transformed *Bifidobacterium* is orally administered, the GL-BP-WT1 fusion protein expressed on the surface of the *Bifidobacterium* is taken up by gut-associated lymphoid tissue (GALT) and processed with an appropriate epitope by an antigen-presenting cell (APC) in the GALT. Further, it is considered that a peptide subjected to the processing in the GALT is displayed on the APC together with MHC class II to induce a CTL having a T cell receptor specific to the peptide. H-2db WT1 Tetramer-RMFPNAPYL binds to a T cell receptor specific to a CD8 epitope (a.a. 126-134: RMFPNAPYL (SEQ ID NO: 19)), which is one of the epitopes contained in the WT1 protein, to emit fluorescence, and hence enables the confirmation of the induction of the CTL specific to the CD8 epitope. It was found from the results of FIG. 8 that the ratio of WT1 tetramer-positive CTLs in the splenocytes in the *B. longum* 420-administered group significantly increased as compared to those in the other administered groups (*; p<0.05). Therefore, it was shown that the GL-BP-WT1 fusion protein of the orally administered transformed *Bifidobacterium* was appropriately processed to induce WT1 peptide-specific CTLs playing an important role in anti-tumor effect.

(4) For splenocytes prepared in the same manner as in the section (1), the activity of WT1-specific cytotoxic T cells (CTLs) was measured.

$3 \times 10^7$ cells/well of the murine splenocytes (n=5) were mixed with $3 \times 10^6$ cells/well of the C1498-WT1 cells, and the cells were cultured in a 6-well plate under the conditions of 37° C. and 5% $CO_2$ for 6 days. On the 1st day and the 3rd day of the culture, 20 IU/ml of IL-2 was added to induce CTLs. The splenocytes were recovered. In a 96-well plate, the splenocytes were mixed with $1 \times 10^4$ cells/well of the C1498-WT1 cells or the C1498-Mock cells at a ratio of 20:1, 10:1, or 5:1, and then the cells were cultured under the conditions of 37° C. and 5% $CO_2$ for 8 hours. The culture supernatant was recovered, and lactate dehydrogenase activity in the culture supernatant was measured using Cytotox 96 Non-radioactive Citotoxicity Assay Kit (Promega). On the basis of the measured activity, cytotoxic activity was calculated. Lactate dehydrogenase is an enzyme present in the cytoplasm. Lactate dehydrogenase normally does not permeate the cell membrane, but is released into the medium when the cell membrane is injured. Therefore, lactate dehydrogenase is used as an indicator for cytotoxic activity.

Figure 9:
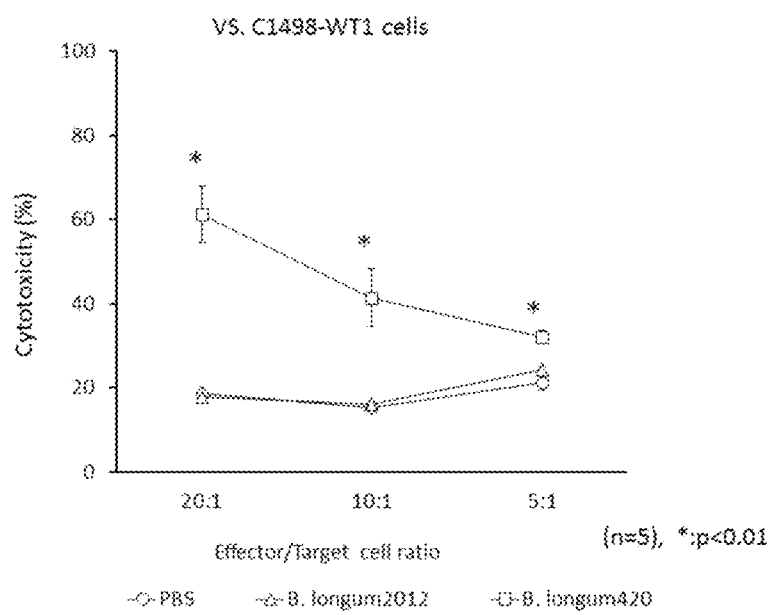
FIG. 9 are graphs for showing results of confirmation of the WT1-specific cytotoxic activation capacity of the transformed *Bifidobacterium* of the present invention (Example 3).
Figure 9:
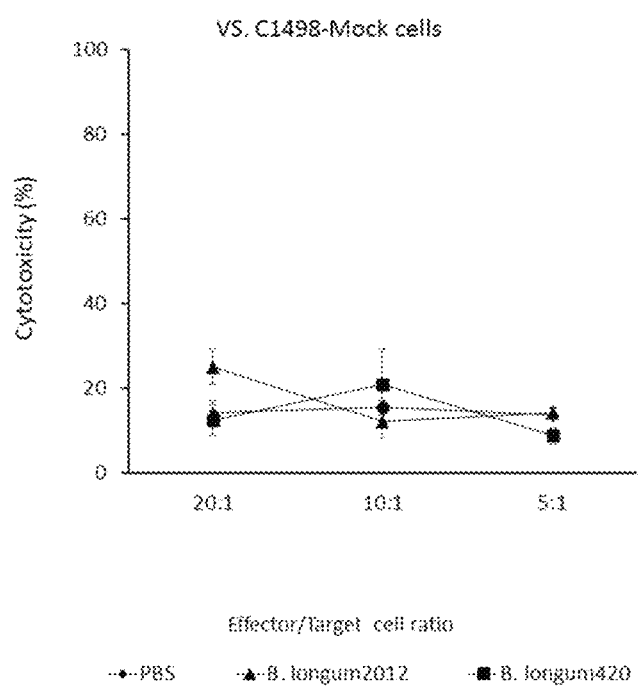

The results are shown in FIG. 9. In all the cell mixing ratios, WT1-specific cytotoxic activity in the *B. longum* 420-administered group significantly increased (p<0.01). Thus, it was found that the oral administration of the GL-BP-WT1 fusion protein of the transformed *Bifidobacterium* induced CTLs having WT1-specific cytotoxic activity.

Example 4: Generation of *Bifidobacterium* Displaying GL-BP-WT1 on Surface Thereof 2

A. the isolation of a GL-BP gene and B. the construction of a pMW118 plasmid having an isolated GL-BP gene were performed by the same techniques as those of Example 1.

C. Isolation of WT1 Gene

DNA encoding an amino acid sequence from position 117 to position 439 (SEQ ID NO: 14) of human WT1 (SEQ ID NO: 15) was obtained by total synthesis (Funakoshi Co., Ltd.). In the synthesis, codons frequently used in a *Bifidobacterium* were used. In addition, an XhoI recognition sequence (CTCGAG: SEQ ID NO: 5) was added to the N-terminus side, and a stop codon and a succeeding SphI recognition sequence (GCATGC: SEQ ID NO: 6) were added to the C-terminus side. The DNA was introduced into the SmaI site of a pUC18 vector to construct a plasmid. DNA Ligation Kit Ver. 2 (manufactured by Takara Bio Inc.) was used for ligation. The constructed plasmid was transferred into *E. coli* DH5a (manufactured by Takara Bio Inc.) by a heat shock method (42° C., 30 seconds). The resultant was applied to an LB agar medium containing 100 μg/ml of ampicillin (manufactured by Difco), and was cultured at 37° C. overnight to provide transformed *E. coli* harboring a plasmid having DNA encoding a human WT1 protein (117 to 439). The plasmid was extracted and purified from the transformed *E. coli* using Quantum Prep Plasmid Miniprep Kit (manufactured by Bio-Rad), and its sequence was confirmed by sequencing.

```
Sequence of synthesized human WT1 gene
                                        (SEQ ID NO: 15)
CCGTCCCAGGCGTCGTCGGGCCAGGCGAGGATGTTCCCGAACGCGCCC

TACCTGCCCAGCTGCCTGGAGTCCCAGCCGGCGATCCGCAACCAGGGC

TACTCCACCGTGACGTTCGACGGCACCCCGTCCTACGGCCACACGCCC

AGCCACCACGCCGCCCAGTTCCCGAACCACAGCTTCAAGCACGAAGAC

CCCATGGGCCAGCAGGGCAGCCTCGGCGAACAGCAGTACAGCGTGCCG

CCGCCGGTCTACGGCTGCCACACCCCGACCGACTCCTGCACGGGCTCC

CAGGCCCTGCTCCTGCGTACGCCGTACTCCTCCGACAACCTCTACCAG

ATGACCTCCCAGCTGGAGTGCATGACCTGGAACCAGATGAACCTGGGC

GCCACGCTGAAGGGAGTCGCCGCGGGGTCGTCGAGCTCCGTCAAGTGG

ACCGAAGGCCAGTCCAACCACTCCACCGGCTACGAGTCCGACAACCAC

ACCACGCCGATCCTGTGCGGAGCCCAGTACCGCATCCACACGCACGGC

GTCTTCCGCGGCATCCAGGACGTCCGGCGCGTCCCCGGCGTCGCGCCG

ACCCTGGTGCGGTCCGCCTCCGAGACCTCCGAGAAGCGCCCGTTCATG

TGCGCCTACCCGGGCTGCAACAAGCGCTACTTCAAGCTCTCGCACCTG

CAGATGCACTCCCGGAAGCACACCGGCGAGAAGCCGTACCAGTGCGAC
```

-continued

```
TTCAAGGACTGCGAACGCCGCTTCTCGCGCAGCGACCAGCTGAAGCGC

CACCAGCGTAGGCACACCGGCGTGAAGCCCTTCCAGTGCAAGACCTGC

CAGCGCAAGTTCTCCCGCAGCGACCACCTCAAGACGCACACCCGCACC

CACACCGGCAAGACGTCCGAGAAGCCGTTCTCGTGCCGCTGGCCCAGC

TGCCAGAAGAAGTTCGCCCGCAGCGACGAGCTCGTGCGCCACCACAAC

ATGCACCAGTGAA
```

In addition, DNA encoding a mutant WT1 protein having an amino acid sequence having a M236Y substitution introduced into an HLA-A*2402-restrictive CTL epitope in an amino acid sequence from position 117 to position 439 of human WT1 (SEQ ID NO: 16) was obtained by total synthesis in the same manner as above, and a recombinant plasmid was generated.

```
Sequence of synthesized human WT1 gene
                                      (SEQ ID NO: 17)
CCGTCCCAGGCGTCGTCGGGCCAGGCGAGGATGTTCCCGAACGCGCCC

TACCTGCCCAGCTGCCTGGAGTCCCAGCCGGCGATQCGCAACCAGGGC

TACTCCACCGTGACGTTCGACGGCACCCCGTCCTACGGCCACACGCCC

AGCCACCACGCCGCCCAGTTCCCGAACCACAGCTTCAAGCACGAAGAC

CCCATGGGCCAGCAGGGCAGCCTCGGCGAACAGCAGTACAGCGTGCCG

CCGCCGGTCTACGGCTGCCACACCCCGACCGACTCCTGCACGGGCTOC

CAGGCCCTGCTCCTGCGTACGCCGTACTCCTCCGACAACCTCTACCAG

ATGACCTCCCAGCTGGAGTGCTACACCTGGAACCAGATGAACCTGGGC

GCCACGCTGAAGGGAGTCGCCGCGGGGTCGTCGAGCTCCGTCAAGTGG

ACCGAAGGCCAGTCCAACCACTCCACCGGCTACGAGTCCGACAACCAC

ACCACGCCGATCCTGTGCGGAGCCCAGTACCGCATCCACACGCACGGC

GTCTTCCGCGGCATCCAGGACGTCCGGCGCGTCCCCGGCGTCGCGCCG

ACCCTGGTGCGGTCCGCCTCCGAGACCTCCGAGAAGCGCCCGTTCATG

TGCGCCTACCCGGGCTGCAACAAGCGCTACTTCAAGCTCTCGCACCTG

CAGATGCACTCCCGGAAGCACACCGGCGAGAAGCCGTACCAGTGCGAC

TTCAAGGACTGCGAACGCCGCTTCTCGCGCAGCGACCAGCTGAAGCGC

CACCAGCGTAGGCACACCGGCGTGAAGCCCTTCCAGTGCAAGACCTGC

CAGCGCAAGTTCTCCCGCAGCGACCACCTCAAGACGCACACCCGCACC

CACACCGGCAAGACGTCCGAGAAGCCGTTCTCGTGCCGCTGGCCCAGC

TGCCAGAAGAAGTTCGCCCGCAGCGACGAGCTCGTGCGCCACCACAAC

ATGCACCAGTGAA
```

D. the construction of a plasmid having a WT1 gene downstream of a GL-BP gene, E. the construction of an *E. coli-Bifidobacterium* shuttle vector, F. the integration of a gene having a GL-BP gene and a WT1 gene linked to each other into an *E. coli-Bifidobacterium* shuttle vector pJW241, and G. the preparation of a host *Bifidobacterium* liquid were performed in the same manner as in Example 1 to generate two kinds of transformed *Bifidobacterium*.

Figure 10:
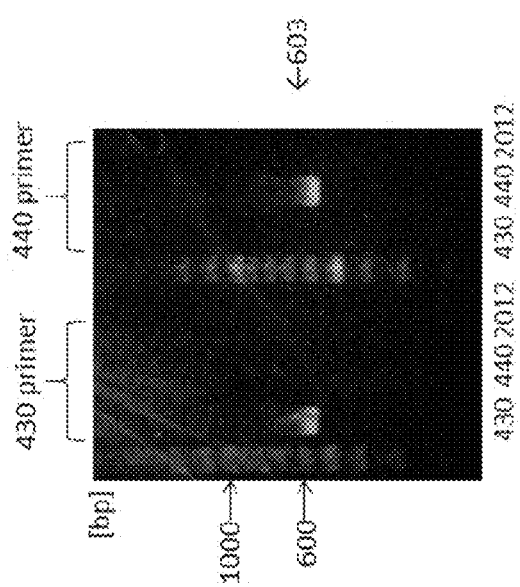
FIG. 10 is an image for showing results of confirmation of DNA encoding a WT1 protein at the gene level in the transformed *Bifidobacterium* of the present invention (Example 4).
Figure 10:
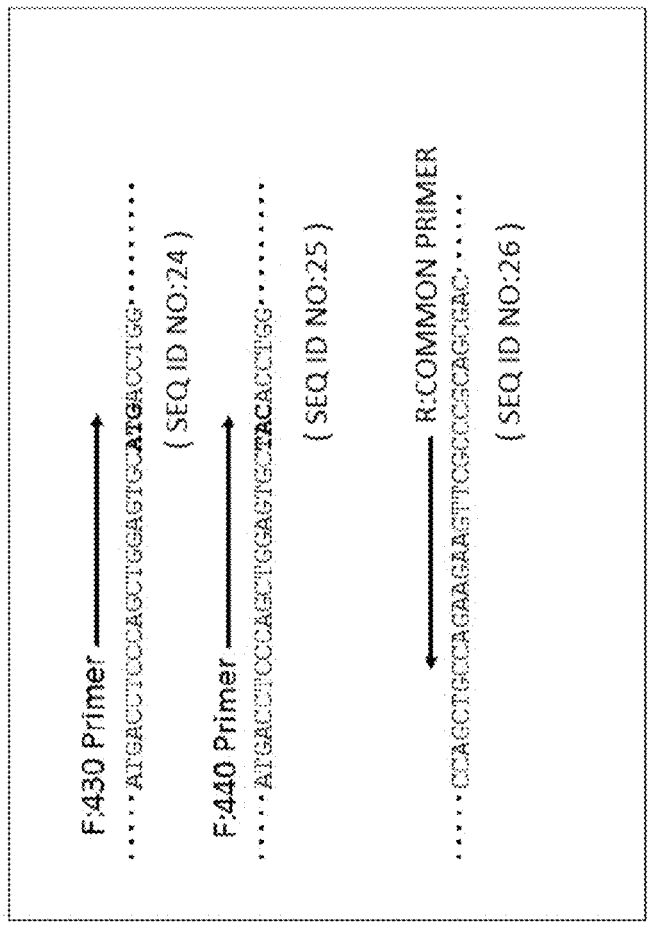

FIG. 10 is an image for showing that the two kinds of transformed *Bifidobacterium* were identified at the gene level using specific primers shown on the right-hand side of FIG. 10. 430 represents *B. longum* 430, which is a *Bifidobacterium* transformed with a shuttle vector having inserted therein DNA encoding a human WT1 protein (117 to 439). 440 represents *B. longum* 440, which is a *Bifidobacterium* transformed with a shuttle vector having inserted therein DNA encoding a human WT1 protein (117 to 439) having an amino acid substitution M236Y. As in Example 1, 2012 represents *B. longum* 2012, which is a *Bifidobacterium* transformed with a shuttle vector having inserted therein only a GLBP gene without having inserted therein DNA encoding WT1. The primer denoted by 430 amplifies the DNA encoding the human WT1 protein (117 to 439), and the primer denoted by 440 amplifies the DNA encoding the human WT1 protein (117 to 439) having an amino acid substitution M236Y.

Example 5: Confirmation of Displaying of GL-BP-WT1 Fusion Protein of Transformed *Bifidobacterium* on Surface Thereof For each transformed *Bifidobacterium* obtained in Example 4 described above, the expression of the GL-BP-WT1 fusion protein on the surface thereof was confirmed by the same technique as that of Example 2.

Figures 11A, 11B:
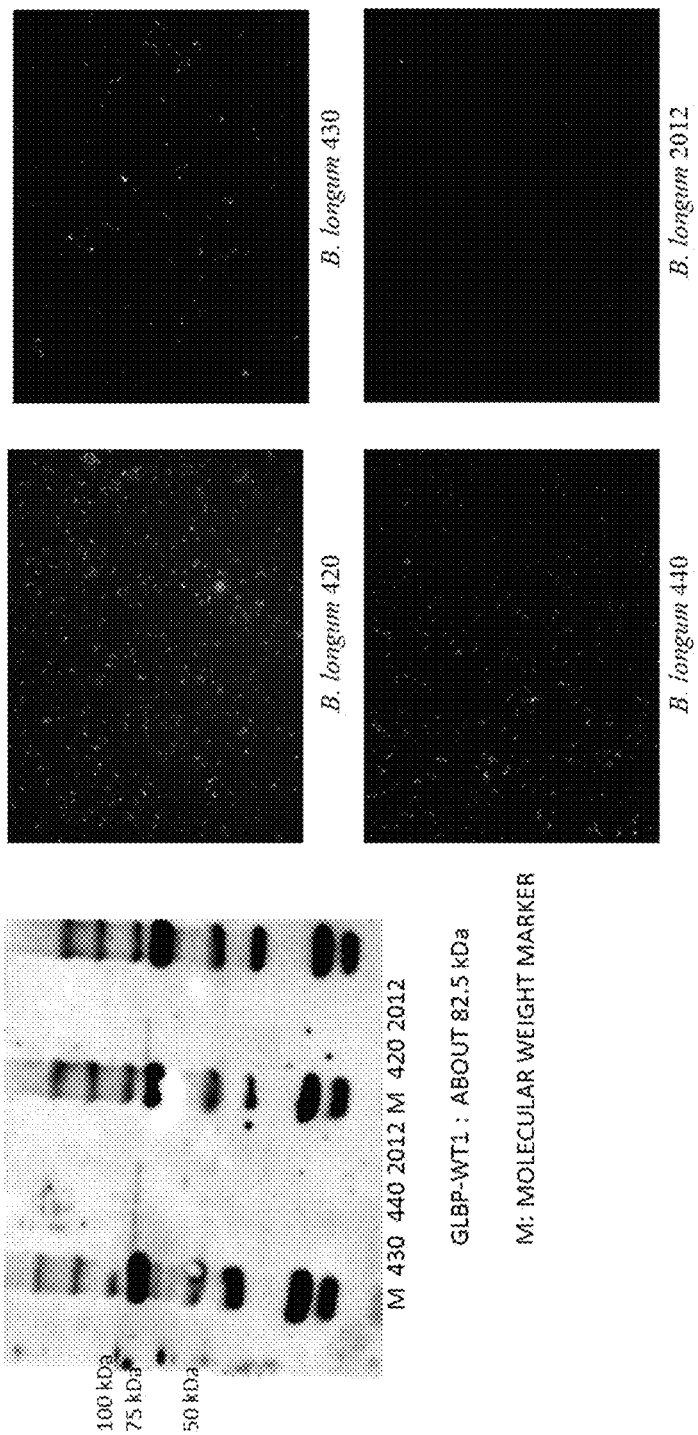
FIGS. 11A and 11B are photographic images for showing: results of confirmation by western blotting of a WT1 protein expressed on the surface of the transformed *Bifidobacterium* of the present invention (FIG. 11A); and results of confirmation thereof by immunofluorescence staining (FIG. 11B) (Example 5).

The results of western blotting are shown in FIG. 11A, and the results of immunofluorescence staining are shown in FIG. 11B. As apparent from FIGS. 11A and 11B, *B. longum* 430 and *B. longum* 440 each showed a band at about 82.5 kDa corresponding to the sum of the molecular weights of WT1 and the GL-BP fusion protein as with *B. longum* 420. In addition, it was confirmed from the fluorescence micrographs that WT1 was present on the cell surface of each of *B. longum* 430 and *B. longum* 440. Therefore, it was confirmed that each transformed *Bifidobacterium* expressed a GL-BP-WT1 fusion protein.

Reference Example 1: PD-L1 Expression Analysis of Prostate Cancer Cells by Flow Cytometry A murine prostate cancer cell line TRAMP-C2 was seeded into a 6-well plate at $5×10^5$ cells/well, and cultured under the conditions of 37° C. and 5% $CO_2$ for 24 hours. After that, the medium was changed to one supplemented with 0 ng/mL, 5 ng/mL, 10 ng/mL, or 20 ng/mL of IFN-γ having a PD-L1 expression-inducing action, and the cells were cultured under the conditions of 37° C. and 5% $CO_2$ for 48 hours. The cells were washed with PBS, and the cells were recovered and then subjected to blocking for 10 minutes using Purified anti-mouse CD16/32 (BioLegend). The detection of PD-L1 was performed using a flow cytometer (Guava easycyte; Merck Millipore) after a reaction with an FITC-labeled anti-PD-L1 monoclonal antibody (PE anti-mouse CD274; BioLegend) for 30 minutes and washing with PBS. Data analysis was performed with InCyte Software. A specific method performed was in conformity to the manual of the kit.

Figure 12:
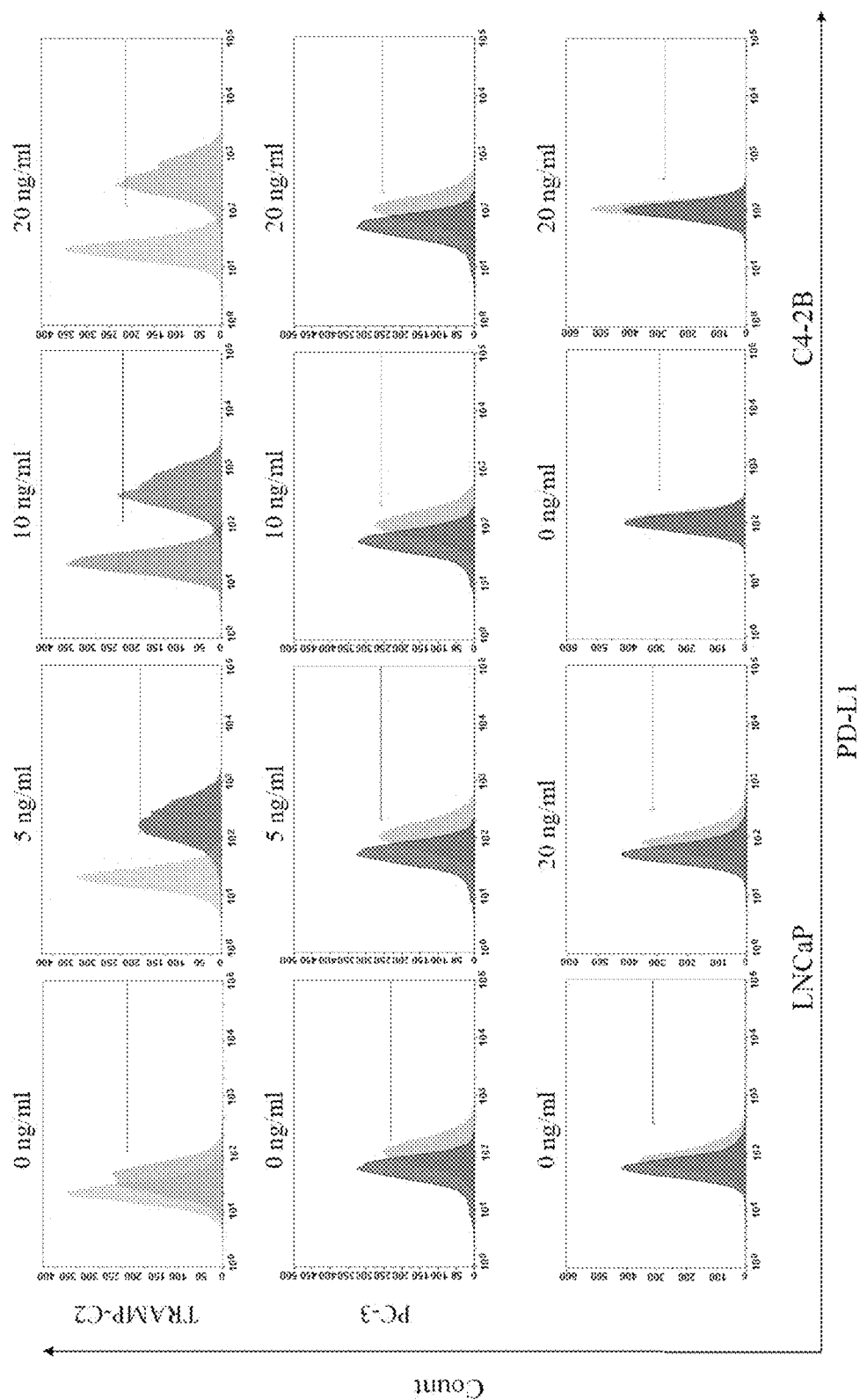
FIG. 12 are graphs for showing results of analysis of prostate cancer cells for the expression amount of PD-L1 by a flow cytometry method (Reference Example 1).

The results are shown in FIG. 12. It was confirmed that, in the murine prostate cancer cell line TRAMP-C2, the expression amount of PD-L1 increased in a manner dependent on an increase in concentration of IFN-γ. PD-L1 was detected in: 0.24% of the cells at 0 ng/ml of IFN-γ supplementation; 65.49% of the cells at 5 ng/ml; 91.92% of the cells at 10 ng/ml; and 91.31% of the cells at 20 ng/ml.

Example 6: Confirmation of Anti-Tumor Effect of Combined Use of Transformed *Bifidobacterium* with Immune Checkpoint Inhibitor Murine prostate cancer cells TRAMP-C2 were transplanted by subcutaneous inoculation into C57BL/6N mice (6- to 8-week-old, male, n=45) at 2×10⁶ cells/200 µL RPMI-1640/Matrigel. After tumor formation had been confirmed, the mice were assigned into the following seven administered groups, and administration was initiated.

PBS-administered group (n=9)
B. longum 2012-administered group (n=8)
B. longum 2012+anti-PD1 antibody-administered group (n=5)
B. longum 2012+Isotype control-administered group (n=5)
B. longum 420-administered group (n=8)
B. longum 420+anti-PD1 antibody-administered group (n=5)
B. longum 420+Isotype control-administered group (n=5)

Figure 13:
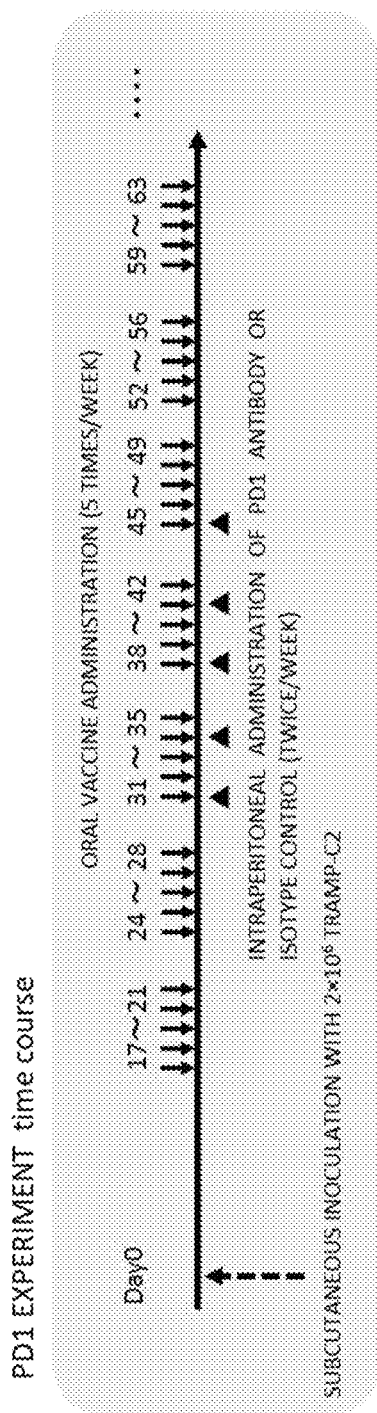
FIG. 13 is a diagram for illustrating an experimental protocol for confirming the anti-tumor effect of the combined use of the transformed *Bifidobacterium* of the present invention with an immunosuppression inhibitor through the use of mice (Example 6).

An administration schedule is described (FIG. 13). Each Bifidobacterium administration liquid at 1×10⁹ CFU/100 µL, or 100 µL of PBS was orally administered to the mice 5 times a week using a sonde. After 2 weeks from the initiation of the oral administration, the combined use of an anti-PD1 antibody (Armenian hamster IgG2 (clone: AP-MAB0839, Angio-Protepmie, Boston, Mass.)) or an isotype control (Hamster IgG2 isotype control (BioLegend)) was initiated. The anti-PD1 antibody or the isotype control was intraperitoneally administered at 100 µg/dose in 100 µL PBS twice a week, a total of 5 times. The day of the transplantation was defined as Day 0, and a tumor size was confirmed.

Figure 14:
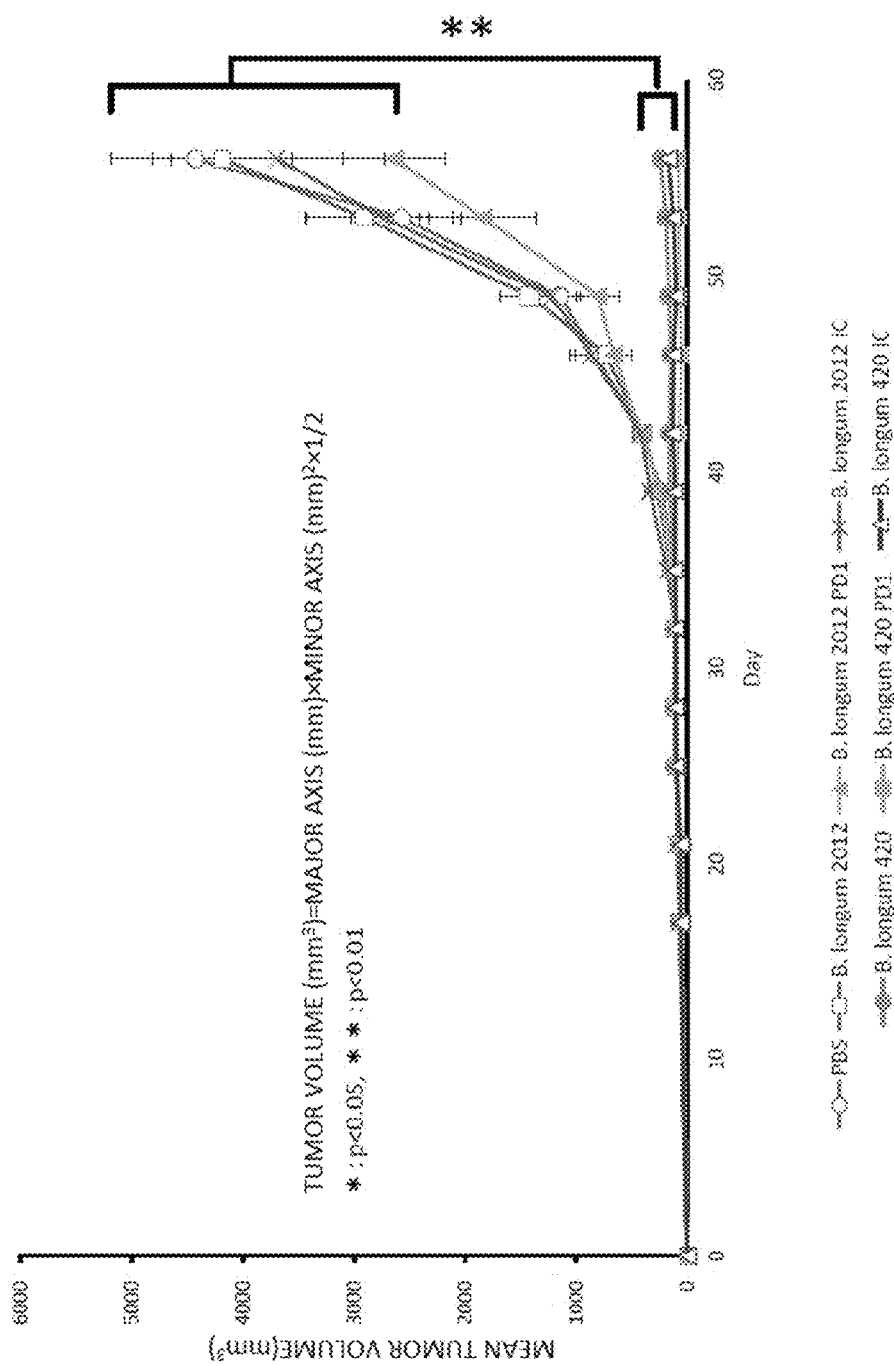
FIG. 14 is a graph for showing results of confirmation of the anti-tumor effect of the combined use of the transformed *Bifidobacterium* of the present invention with the immunosuppression inhibitor (Example 6).
Figure 15:
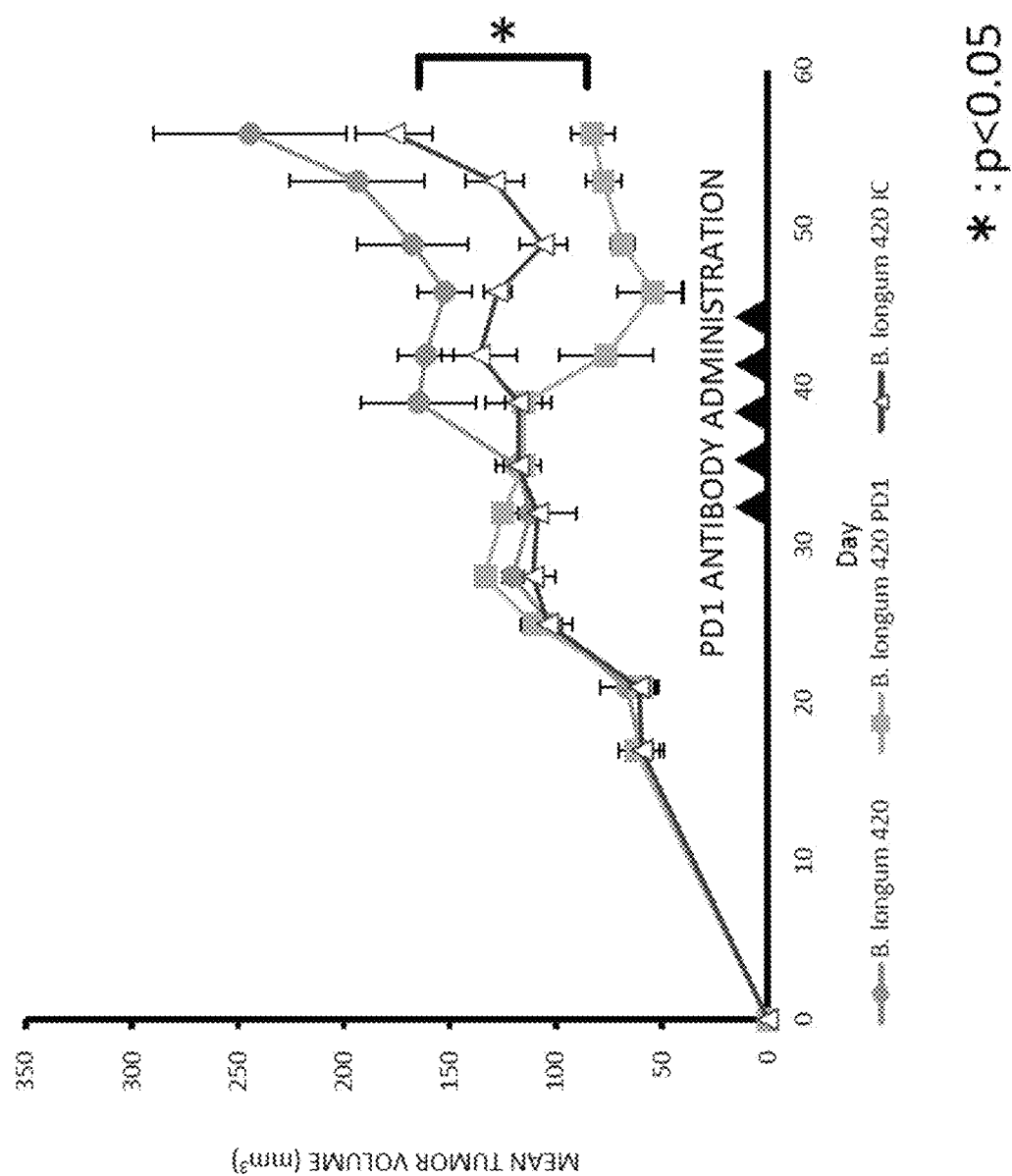
FIG. 15 is a graph for showing results of confirmation of the anti-tumor effect of the combined use of the transformed *Bifidobacterium* of the present invention with the immunosuppression inhibitor (Example 6).

Changes over days in tumor size in the respective administered groups are shown in FIG. 14 and FIG. 15. In FIG. 14 and FIG. 15, the PBS-administered group is represented by "PBS", the B. longum 2012-administered group is represented by "B. longum 2012", the B. longum 2012+anti-PD1 antibody-administered group is represented by "B. longum 2012 PD1", the B. longum 2012+Isotype control-administered group is represented by "B. longum 2012 IC", the B. longum 420-administered group is represented by "B. longum 420", the B. longum 420+anti-PD1 antibody-administered group is represented by "B. longum 420 PD1", and the B. longum 420+Isotype control-administered group is represented by "B. longum 420 IC". FIG. 15 is an extract of the results of the B. longum 420-administered group, the B. longum 420+anti-PD1 antibody-administered group, and the B. longum 420+anti-PD1 antibody-administered group from FIG. 14.

All the groups administered with B. longum 420 showed significant anti-tumor effects (p<0.01) as compared to the groups not administered with B. longum 420 (the PBS-administered group, the B. longum 2012-administered group, the B. longum 2012+anti-PD1 antibody-administered group, and the B. longum 2012+Isotype control-administered group) (FIG. 14). In addition, on Day 56 (last day of the graph of FIG. 15), three groups, i.e., the B. longum 420-administered group, the B. longum 420+anti-PD1 antibody-administered group, and the B. ion gum 420+Isotype control-administered group were compared to each other, and as a result, it was confirmed that the B. longum 420+anti-PD1 antibody-administered group showed a significant tumor reduction with respect to the group administered with B. longum 420 alone (p<0.05) (FIG. 15). Thus, a remarkable combined use effect of the transformed Bifidobacterium of the present invention and the anti-PD1 antibody was confirmed.

Example 7: Confirmation of Anti-Tumor Effect of Combined Use of Transformed Bifidobacterium with Immune Checkpoint Inhibitor Murine prostate cancer cells TRAMP-C2 were transplanted by subcutaneous inoculation into C57BL/6N mice (6- to 8-week-old, male) at 2×10⁶ cells/200 µL RPMI-1640/Matrigel. After tumor formation had been confirmed, a total of 56 mice were assigned into the following seven administered groups (7 mice per group), and administration was initiated.

Figure 16:
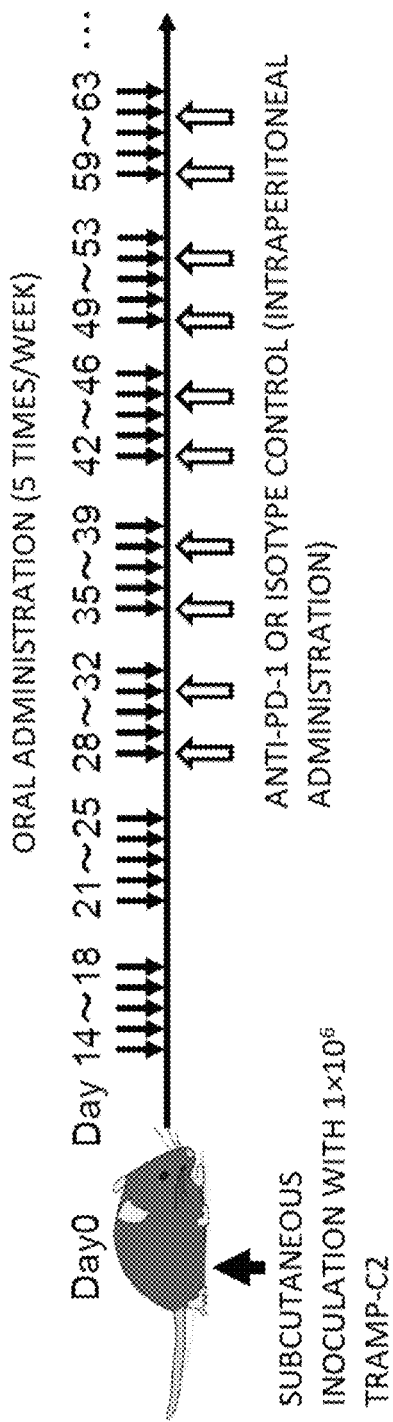
FIG. 16 is a diagram for illustrating an experimental protocol for confirming the anti-tumor effect of the combined use of the transformed *Bifidobacterium* of the present invention with an immunosuppression inhibitor through the use of mice (Example 7).

PBS-administered group (100 µL)
B. longum 2012 (1×10⁹ CFU/100 µL)-administered group
B. longum 2012+anti-PD-1 antibody (250 µg; InvivoPlus anti-mouse PD-1: RMP1-14)-administered group
B. longum 2012+Isotype control (250 µg; InvivoPlus Rat IgG2a Isotype Control: 2A3)-administered group
B. longum 420 (1×10⁹ CFU/100 µL)-administered group
B. longum 420+anti-PD-1 antibody (250 µg; InvivoPlus anti-mouse PD-1: RMP1-14)-administered group
B. longum 420+Isotype control (250 µg; InvivoPlus Rat IgG2a Isotype Control: 2A3)-administered group An administration schedule is described (FIG. 16). Each Bifidobacterium administration liquid at 1×10⁹ CFU/100 µL, or 100 µL of PBS was orally administered to the mice 5 times a week using a sonde. After 2 weeks from the initiation of the oral administration, the combined use of an anti-PD1 antibody (InvivoPlus anti-mouse PD-1: RMP1-14 (Bio X Cell)) or an isotype control (InvivoPlus Rat IgG2a Isotype Control: 2A3 (Bio X Cell)) was initiated. The anti-PD1 antibody or the isotype control was intraperitoneally administered at 250 µg/dose in 100 µL PBS twice a week, a total of 5 times. The day of the transplantation was defined as Day 0, and a tumor size was confirmed.

Figure 17A:
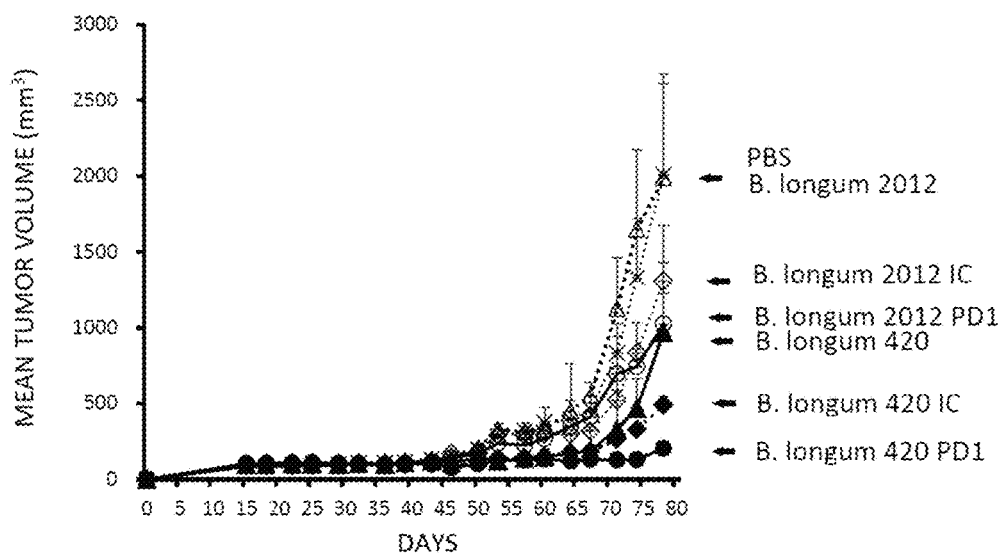
FIGS. 17A and 17B are graphs for showing results of confirmation of the anti-tumor effect of the combined use of the transformed *Bifidobacterium* of the present invention with the immunosuppression inhibitor. Changes over days in tumor size (tumor curves) up to 80 days from transplantation are shown in FIG. 17A, and survival curves of mice up to the 100th day from transplantation are shown in FIG. 17B (Example 7).
Figure 17B:
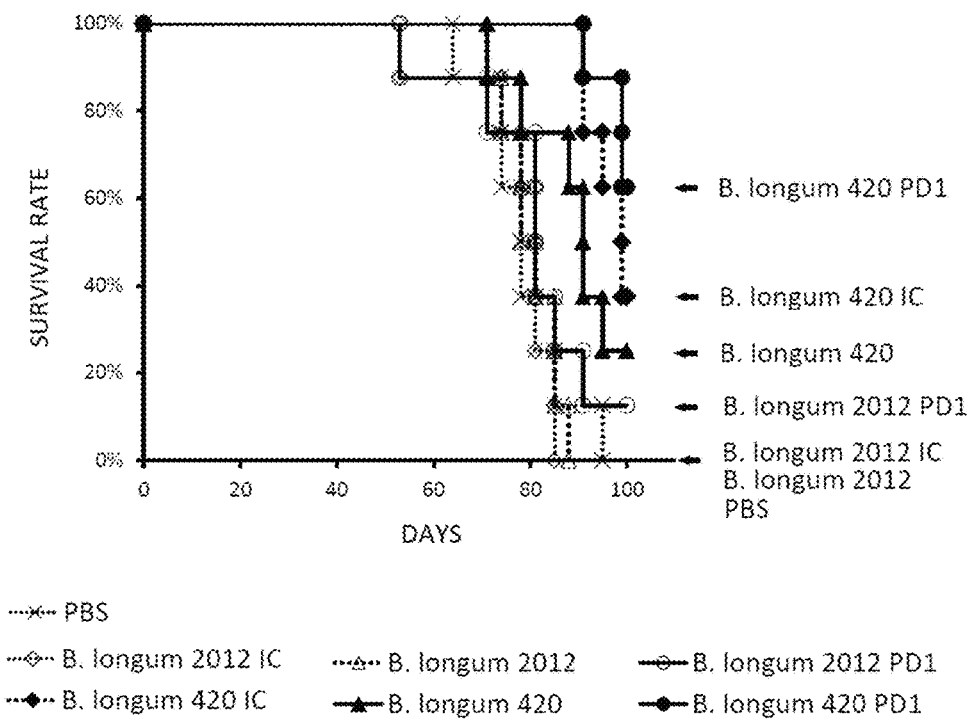

Changes over days in tumor size (tumor curves) up to 80 days from transplantation in the respective administered groups are shown in FIG. 17A, and survival curves of the mice up to the 100th day from transplantation are shown in FIG. 17B. In FIG. 17A and FIG. 17B, the PBS-administered group is represented by "PBS", the B. longum 2012-administered group is represented by "B. longum 2012", the B. longum 2012+anti-PD1 antibody-administered group is represented by "B. longum 2012 PD1", the B. longum 2012+Isotype control-administered group is represented by "B. longum 2012 IC", the B. longum 420-administered group is represented by "B. longum 420", the B. longum 420+anti-PD1 antibody-administered group is represented by "B. longum 420 PD1", and the B. longum 420+Isotype control-administered group is represented by "B. longum 420 IC". In the foregoing, 420 represents B. longum 420, which is a Bifidobacterium transformed with a shuttle vector having inserted therein DNA encoding murine WT1 (aa 117 to 439), and 2012 represents B. longum 2012, which is a Bifidobacterium transformed with a shuttle vector having inserted therein only a GLBP gene without having inserted therein DNA encoding murine WT1 (see Example 1).

All the groups administered with B. longum 420 showed significant anti-tumor effects as compared to the groups not administered with B. longum 420 (the PBS-administered group, the B. longum 2012-administered group, the B. longum 2012+anti-PD1 antibody-administered group, and the B. longum 2012+Isotype control-administered group), and it was confirmed that the B. longum 420+anti-PD1 antibody-administered group showed a significant tumor reduction with respect to the group administered with B. longum 420 alone (FIG. 17A and FIG. 17B). Thus, a remarkable combined use effect of the transformed Bifidobacterium of the present invention and the anti-PD1 antibody was confirmed.

INDUSTRIAL APPLICABILITY

As described in detail above, according to the present invention, an excellent anti-tumor effect can be exhibited through the combined use of the transformed *Bifidobacterium* capable of expressing and displaying the WT1 protein with the immunosuppression inhibitor. It is considered that cancer can even be caused to disappear by continuing the combined use of the transformed *Bifidobacterium* of the present invention with the immunosuppression inhibitor. In addition, the transformed *Bifidobacterium* of the present invention can be used as a highly safe oral vaccine, and hence can minimize a burden on a patient. Further, the combination therapy of the present invention has low HLA restriction, and hence is widely applicable to patients of various HLA types.

The invention claimed is:

1. An anti-tumor agent comprising an active ingredient, wherein the active ingredient is a tumor vaccine, in combination with an immunosuppression inhibitor, the tumor vaccine comprising a transformed *Bifidobacterium* containing:
   DNA encoding a WT1 protein; and
   DNA encoding a GNB/LNB substrate-binding membrane protein derived from a *Bifidobacterium*, wherein
   the WT1 protein is expressed and displayed on a cell surface of the transformed *Bifidobacterium* as a fusion protein of the WT1 protein and the GNB/LNB substrate-binding membrane protein (GL-BP-WT1 fusion protein).

2. The anti-tumor agent according to claim 1, wherein the immunosuppression inhibitor comprises an immune checkpoint inhibitor, and comprises at least one antibody selected from the group consisting of an anti-PD1 antibody, an anti-PD-L1 antibody, and an anti-CTLA4 antibody.

3. The anti-tumor agent according to claim 1, wherein the immunosuppression inhibitor comprises an anti-PD1 antibody.

4. The anti-tumor agent according to claim 1, wherein the WT1 protein displayed on the cell surface of the transformed *Bifidobacterium* comprises a protein identified by an amino acid sequence identified by SEQ ID NO: 1.

5. The anti-tumor agent according to claim 1, wherein the DNA encoding the WT1 protein displayed on the cell surface of the transformed *Bifidobacterium* comprises DNA having a base sequence identified by SEQ ID NO: 2.

6. The anti-tumor agent according to claim 1, wherein the WT1 protein displayed on the cell surface of the transformed *Bifidobacterium* comprises a protein identified by an amino acid sequence identified by SEQ ID NO: 14 or SEQ ID NO: 16.

7. The anti-tumor agent according to claim 1, wherein the transformed *Bifidobacterium* further contains DNA encoding a protein having an adjuvant function between the DNA encoding the WT1 protein and the DNA encoding the GNB/LNB substrate-binding membrane protein derived from a *Bifidobacterium*.

8. The anti-tumor agent according to claim 1, wherein the tumor vaccine is an oral formulation.

9. The anti-tumor agent according to claim 1, wherein the transformed *Bifidobacterium* comprises an inactivated transformed *Bifidobacterium*.

10. An anti-tumor agent comprising an active ingredient in combination with an immunosuppression inhibitor, the active ingredient comprising a transformed *Bifidobacterium* having a WT1 protein expressed and displayed thereon as a fusion protein of the WT1 protein and the GNB/LNB substrate-binding membrane protein (GL-BP-WT1 fusion protein).

11. The anti-tumor agent according to claim 10, wherein the anti-tumor agent has an anti-tumor effect on solid cancer.

12. The anti-tumor agent according to claim 10, wherein the anti-tumor agent has an anti-tumor effect on prostate cancer.

13. The anti-tumor agent according to claim 10, wherein the immunosuppression inhibitor comprises an immune checkpoint inhibitor, and comprises at least one antibody selected from the group consisting of an anti-PD1 antibody, an anti-PD-L1 antibody, and an anti-CTLA4 antibody.

14. The anti-tumor agent according to claim 10, wherein the immunosuppression inhibitor comprises an anti-PD1 antibody.

15. The anti-tumor agent according to claim 10, wherein the WT1 protein displayed on the cell surface of the transformed *Bifidobacterium* comprises a protein identified by an amino acid sequence identified by SEQ ID NO: 1.

16. The anti-tumor agent according to claim 10, wherein the WT1 protein displayed on the cell surface of the transformed *Bifidobacterium* comprises a protein identified by an amino acid sequence identified by SEQ ID NO: 14 or SEQ ID NO: 16.

17. The anti-tumor agent according to claim 10, wherein the active ingredient is a tumor vaccine.

18. The anti-tumor agent according to claim 17, wherein the transformed *Bifidobacterium* comprises an inactivated transformed *Bifidobacterium*.

19. The anti-tumor agent according to claim 17, wherein the tumor vaccine is an oral formulation.

20. The anti-tumor agent according to claim 3, wherein the anti-PD1 antibody is at least one of nivolumab, pembrolizumab, and pidilizumab.

* * * * *